(12) United States Patent
Evans et al.

(10) Patent No.: US 7,208,300 B2
(45) Date of Patent: Apr. 24, 2007

(54) MEMBER OF THE LYSYL OXIDASE GENE FAMILY

(75) Inventors: Mark J. Evans, Radnor, PA (US); Marshall S. Scicchitano, Douglasville, PA (US); Ashok R. Bapat, Blue Bell, PA (US); Ramesh A. Bhat, King of Prussia, PA (US); Robert Mastroeni, Plymouth Meeting, PA (US); Sotirios K. Karathanasis, Saline, MI (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/924,946

(22) Filed: Aug. 8, 2001

(65) Prior Publication Data

US 2002/0102645 A1  Aug. 1, 2002

Related U.S. Application Data

(60) Provisional application No. 60/255,838, filed on Dec. 15, 2000, provisional application No. 60/223,763, filed on Aug. 8, 2000.

(51) Int. Cl.
| | |
|---|---|
| C12N 9/02 | (2006.01) |
| C12N 15/00 | (2006.01) |
| C12N 1/20 | (2006.01) |
| C12Q 1/00 | (2006.01) |
| C12Q 1/68 | (2006.01) |
| C12Q 21/04 | (2006.01) |
| C07H 21/04 | (2006.01) |

(52) U.S. Cl. .......................... 435/189; 435/440; 435/4; 435/6; 435/252.3; 435/320.1; 435/69.1; 435/71.1; 536/23.2; 536/23.1; 536/23.7; 536/23.74

(58) Field of Classification Search ................ 435/190, 435/252.3, 320.1, 71.1, 440, 189, 6, 4, 69.1, 435/23.2, 23.1; 536/23.2, 24.3, 23.1, 23.7, 536/23.74; 530/350
See application file for complete search history.

(56) References Cited

U.S. PATENT DOCUMENTS

| 5,945,279 A | 8/1999 | O'Malley et al. ............... 435/6 |
| 2002/0068322 A1* | 6/2002 | Meyers ....................... 435/69.1 |
| 2003/0059919 A1 | 3/2003 | Meyers et al. |

FOREIGN PATENT DOCUMENTS

| WO | 00/37681 | 6/2000 |
| WO | 00/61774 | 10/2000 |
| WO | 01/83702 | 5/2001 |

(Continued)

OTHER PUBLICATIONS

Bonaldo et al. Genome Res. 6 (9), 791-806. 1996. Abstract and sequence alignment.*

(Continued)

*Primary Examiner*—Ponnathapu Achutamurthy
*Assistant Examiner*—Yong D. Pak
(74) *Attorney, Agent, or Firm*—Darby & Darby

(57) ABSTRACT

The present invention relates to a novel lysyl oxidase genes, termed EER-7. The invention relates to the protein and nucleic acids encoding the protein. The invention further relates to an assay system to identify compounds that selectively modulate EER-7 protein activity by interaction with estrogen receptors.

26 Claims, 4 Drawing Sheets

Percent Similarity

| | 1 | 2 | 3 | 4 | 5 | 6 | 7 | 8 | 9 | 10 | | |
|---|---|---|---|---|---|---|---|---|---|---|---|---|
| 1 | | 28.4 | 14.8 | 27.7 | 13.7 | 43.7 | 15.9 | 16.7 | 63.5 | 57.0 | 1 | rabbit EER-7 protein frags pro |
| 2 | 13.7 | | 50.9 | 31.7 | 19.9 | 17.2 | 18.3 | 10.5 | 7.1 | 12.2 | 2 | EER-7 consensus protein.PRO |
| 3 | 95.1 | 70.5 | | 39.6 | 14.1 | 14.3 | 14.9 | 15.1 | 6.1 | 11.5 | 3 | human ws914 protein.PRO |
| 4 | 0.0 | 43.9 | 11.0 | | 38.0 | 69.2 | 59.2 | 60.5 | 59.7 | 65.2 | 4 | mouse ws914 contig1 protein.PRO |
| 5 | 1000.0 | 222.0 | 254.0 | 161.2 | | 51.1 | 49.4 | 49.8 | 27.0 | 31.0 | 5 | human lysyl oxidase like protein.PRO |
| 6 | 0.0 | 76.0 | 85.3 | 80.6 | 2.0 | | 64.9 | 66.2 | 75.2 | 79.3 | 6 | mouse LOL protein.PRO |
| 7 | 0.0 | 178.8 | 190.7 | 159.1 | 87.3 | 33.4 | | 91.8 | 47.2 | 51.1 | 7 | human lysyl oxidase protein PRO |
| 8 | 0.0 | 172.2 | 185.8 | 151.4 | 86.3 | 30.4 | 14.5 | | 48.0 | 51.8 | 8 | mouse lysyl oxidase protein PRO |
| 9 | 0.0 | 97.3 | 67.4 | 56.6 | 117.5 | 117.5 | 140.9 | 140.9 | | 92.6 | 9 | human contig2 est protein PRO |
| 10 | 0.0 | 56.6 | 40.8 | 23.7 | 72.7 | 72.7 | 81.4 | 84.5 | 10.8 | | 10 | mouse contig2 protein PRO |
| | 1 | 2 | 3 | 4 | 5 | 6 | 7 | 8 | 9 | 10 | | |

Percent Divergence

FOREIGN PATENT DOCUMENTS

WO     01/92495     12/2001

OTHER PUBLICATIONS

Ngo et al. The Protein Folding Problem and Tertiary Structure Prediction, 1994, Merz et al. (ed.), Birkhauser, Boston, MA, pp. 433 and 492-495.*

Lascu et al. A point mutation of human nucleoside diphosphate kinase A found in aggressive neuroblastoma affects protein folding. J Biol Chem. Jun. 20, 1997;272(25):15599-602.*

Mitchell et al., Vascular Surgery, 4th edition, 1995, 1032-1060.

Campa, et al., Artheroslerosis, 1987, 65:13-21.

White et al., J. Vasc. Surg., 1993, 17:371-381.

Kagan, Biology of the Extracellular Matrix, 1986, 321-398.

Gacheru et al., J. Biol. Chem., 1990, 265:19022-19027.

Hamalainen et al., Genomics, 1991, 17:544-548.

Mariani et al., *Matrix*, 1992, 12:242-248.

Wu et al., J. Biol. Chem., 1992, 267:24199-24206.

Kenyon et al., Science, 1991, 253:802.

Kenyon et al., J. Biol. Chem., 1993, 268:18435-18437.

Saito et al., J. Biol. Chem., 1997, 272:8157-5160.

Ozasa et al., Endocrinology, 1981, 109:618-621.

Sanada et al., Biochim. Biophys. Acta., 1978, 541:408-413.

Dolores J. Katz, et al., Gender differences in abdominal aortic aneurysm prevalence, treatment, and outcome; *Journal of Vascular Surgery*, vol. 25, No. 3, (Mar. 1997), pp. 561-568.

Singh K., et al., Prevalence of and Risk Factors for Abdominal Aortic Aneurysms in a Population-based Study, *American Journal of Epidemiology*, vol. 154, No. 3, (2001), pp. 236-244.

Brian G. Halloran and B. Timothy Baxter, Pathogenesis of Aneurysms, *Seminars in Vascular Surgery*, vol. 8, No. 2 (Jun. 1995), pp. 85-92.

D M Langenau, et al., The Upregulation of Messenger Ribonucleic Acids During $17\alpha$, $20\beta$-dihydroxy-4-pregnen-3-one-induced Ovulation in the Perch Ovary, *Journal of Molecular Endocrinology*, vol. 23, No. 2, (Oct. 1999), pp. 137-152.

Database EMBL, (Feb. 2000), XP002211809, abstract.

David E. Morales, et al., Estrogen Promotes Angiogenic Activity in Human Umbilical Vein Endothelial Cells in Vitro and in a Murine Model, *American Heart Association*, vol. 91, No. 3, (Feb. 1995), pp. 755-763.

Vicki L. Davis, et al., Aberrant Reproductive Phenotypes Evident In Transgenic Mice Expressing the Wild-Type Mouse Estrogen Receptor, Endocrinology, vol. 135, No. 1, (1994), pp. 379-386.

Hiromu Ito, et al., Molecular Cloning and Biological Activity of a Novel Lysyl Oxidase-related Gene Expressed in Cartilage.

* cited by examiner

Compound 2         Compound 8

SEQUENCE LISTING

<160> NUMBER OF SEQ ID NOS: 11

<210> SEQ ID NO 1
<211> LENGTH: 3616
<212> TYPE: DNA
<213> ORGANISM: Human

<400> SEQUENCE: 1

| | | | | | | |
|---|---|---|---|---|---|---|
| gattatgttg | gggggtcggc | gtgtgacaga | aacaccgaag | ggaaggggc | agaagacttc | 60 |
| aagccccctc | tttcctagcc | tggacaggta | tcttggcctc | agctgtcctt | gaagtcacca | 120 |
| tggcgtggtc | cccaccagcc | accctctttc | tgttcctgct | gctgctaggc | agccccctc | 180 |
| ccagcaggcc | acagtcactg | gcaccacta | agctccggct | ggtgggccca | gagagcaagc | 240 |
| cagaggaggg | ccgcctggag | gtgctgcacc | agggccagtg | gggcaccgtg | tgtgatgaca | 300 |
| actttgctat | ccaggaggcc | acagtggctt | gccgccagct | gggcttcgaa | gctgccttga | 360 |
| cctgggccca | cagtgccaag | tacggccaag | ggagggacc | catctggctg | acaatgtgc | 420 |
| gctgtgtggg | cacagagagc | tccttggacc | agtgcgggtc | taatggctgg | ggagtcagtg | 480 |
| actgcagtca | ctcagaagac | gtaggggtga | tatgccaccc | ccggcgccat | cgtggctacc | 540 |
| tttctgaaac | tgtctccaat | gcccttgggc | cccaggccg | cggctggag | gaggtgcggc | 600 |
| tcaagcccat | ccttgccagt | gccaagcagc | atagcccagt | gaccgaggga | gccgtggagg | 660 |
| tgaagtatga | gggccactgg | cggcaggtgt | gtgaccaggg | ctggaccatg | aacaacagca | 720 |
| gggtggtgtg | cgggatgctg | ggcttcccca | gcgaggtgcc | tgtcgacagc | cactactaca | 780 |
| ggaaagtctg | ggatctgaag | atgagggacc | ctaagtctag | gctgaagagc | ctgacgaata | 840 |
| agaactcctt | ctggatccac | caggtcacct | gcctggggac | agagcccac | atggccaact | 900 |
| gccaggtgca | ggtggctcca | gcccggggca | agctgcggcc | agcctgccca | ggtggcatgc | 960 |
| atgctgtggt | cagctgtgtg | gcagggcctc | acttccgccc | accgaagaca | aagccacaac | 1020 |
| gcaaagggtc | ctgggcagag | gagccgaggg | tgcgcctgcg | ctccggggcc | caggtgggcg | 1080 |
| agggccgggt | ggaagtgctc | atgaaccgcc | agtggggcac | ggtctgtgac | cacaggtgga | 1140 |
| acctcatctc | tgccagtgtc | gtgtgtcgtc | agctgggctt | tggctctgct | cgggaggccc | 1200 |
| tctttgggc | ccggctgggc | caagggctag | ggccatcca | cctgagtgag | gtgcgctgca | 1260 |
| ggggatatga | gcggaccctc | agcgactgcc | ctgccctgga | agggtcccag | aatggttgcc | 1320 |
| aacatgagaa | tgctgctgct | gtcaggtgca | atgtccctaa | catgggcttt | cagaatcagg | 1380 |
| tgcgcttggc | tggtgggcgt | atccctgagg | aggggctatt | ggaggtgcag | gtggaggtga | 1440 |
| acggggtccc | acgctgggg | agcgtgtgca | gtgaaaactg | ggggctcacc | gaagccatgg | 1500 |
| tggcctgccg | acagctcggc | ctgggttttg | ccatccatgc | ctacaaggaa | acctggttct | 1560 |
| ggtcggggac | gccaagggcc | caggaggtgg | tgatgagtgg | ggtgcgctgc | tcaggcacag | 1620 |
| agctggccct | gcagcagtgc | cagaggcacg | gccggtgca | ctgctccac | ggtggcgggc | 1680 |
| gcttcctggc | tggagtctcc | tgcatggaca | gtgcaccaga | cctggtgatg | aacgcccagc | 1740 |
| tagtgcagga | gacggcctac | ttggaggacc | gcccgctcag | ccagctgtat | tgtgcccacg | 1800 |
| aggagaactg | cctctccaag | tctgcggatc | acatggactg | gccctacgga | taccgccgcc | 1860 |
| tattgcgctt | ctccacacag | atctacaatc | tgggccggac | tgactttcgt | ccaaagactg | 1920 |
| gacgcgatag | ctgggtttgg | caccagtgcc | acaggcatta | ccacagcatt | gaggtcttca | 1980 |
| cccactacga | cctcctcact | ctcaatggct | ccaaggtggc | tgagggcac | aaggccagct | 2040 |

-continued

```
tctgtctgga ggacacaaac tgccccacag gactgcagcg gcgctacgca tgtgccaact      2100
ttggagaaca gggagtgact gtaggctgct gggacaccta ccggcatgac attgattgcc      2160
agtgggtgga tatcacagat gtgggccccg ggaattatat cttccaggtg attgtgaacc      2220
cccactatga agtggcagag tcagatttct ccaacaatat gctgcagtgc cgctgcaagt      2280
atgatgggca ccgggtctgg ctgcacaact gccacacagg gaattcatac ccagccaatg      2340
cagaactctc cctggagcag aacagcgtc tcaggaacaa cctcatctga agctgtcact       2400
gcacactcct agctgctgcc gatacaccag atacctcagc ttattggagc catgcccttc      2460
acagagtccc aactcagagg aaaagggcca gtgccaaggg gcaccaagaa cctgctcagg      2520
aagccttttg atggcaagat caccaatcca gatggtattg ctccctcagg atggctctgg      2580
gcctgcccct aagggcctgt ggcctatgga atatgtcctc caggctttgc tcagctgagc      2640
tcctcttctg taaggaaacc cagtcatccc tgaatcttgc cacagagatc cgggattcag      2700
gagctctcag tttcttaggg atggactatg gcccagtccc ccatctaagt ggtgctttgc      2760
aaatgtcttg gaggagtata ggacagagga ccaaaataca cagcaggtag tgttagctct      2820
ctgctaggag ctcaaagcaa cacaacttgt atcaaaatca caactggcag agaagctggt      2880
ggatccaatc ctttcttcat ctgttgttat ttagaactca cctctcacac tctgttcttt      2940
agtgtcctta cctttatctt accacacaca tgggtgtttc tattatcctt ggaagcacag      3000
acctcgggca tccccttatt gcctgatggg ccaacaccaa cagttacgga gtgcttgaga      3060 agggcaagt ttcacagaaa tggccagata gggccttcct acagagcagc aagagtaggc       3120
caagcagaaa gactgctgag gtaacacgga ccccagcccc tgtcagggcc tctgccaagg      3180
aaataatatg gaccatttac ctggcaggca gtctgctctc tctcaggatc accacgcatc      3240
tcaggattgg tctaaacttc aagtctcaac caagtgtctg aagtgaactt tgcattgaat      3300 aaattttgc catggaaaga acatcaaaca agccactcat ctctacagag ataagaaaac       3360
aagtttggca gagcaagaga cagaagaccg tggagaaatc agaaggggga acagtcagtt      3420
tagttaagga tggaacctgg gaaaggccac cattcctgct tgatgggct ctgatttgct       3480 cttgctcaag tggaataaaa ccccatggtc ttcttgacat gattcttgat cttttctcca      3540
ctgagacaca cttaagtgat gatccttaca ggactgacac cctaatgcca ataaaagttg      3600
ctcattatgg actgct                                                     3616
```

<210> SEQ ID NO 2
<211> LENGTH: 756
<212> TYPE: PRT
<213> ORGANISM: Human

<400> SEQUENCE: 2

```
Met Ala Trp Ser Pro Ala Thr Leu Phe Leu Phe Leu Leu Leu Leu
 1               5                  10                  15

Gly Gln Pro Pro Ser Arg Pro Gln Ser Leu Gly Thr Thr Lys Leu
                20                  25                  30

Arg Leu Val Gly Pro Glu Ser Lys Pro Glu Glu Gly Arg Leu Glu Val
            35                  40                  45

Leu His Gln Gly Gln Trp Gly Thr Val Cys Asp Asp Asn Phe Ala Ile
        50                  55                  60

Gln Glu Ala Thr Val Ala Cys Arg Gln Leu Gly Phe Glu Ala Ala Leu
    65                  70                  75                  80

Thr Trp Ala His Ser Ala Lys Tyr Gly Gln Gly Glu Gly Pro Ile Trp
```

-continued

```
                    85                  90                  95
Leu Asp Asn Val Arg Cys Val Gly Thr Glu Ser Ser Leu Asp Gln Cys
                100                 105                 110
Gly Ser Asn Gly Trp Gly Val Ser Asp Cys Ser His Ser Glu Asp Val
                115                 120                 125
Gly Val Ile Cys His Pro Arg Arg His Arg Gly Tyr Leu Ser Glu Thr
                130                 135                 140
Val Ser Asn Ala Leu Gly Pro Gln Gly Arg Arg Leu Glu Glu Val Arg
145                 150                 155                 160
Leu Lys Pro Ile Leu Ala Ser Ala Lys Gln His Ser Pro Val Thr Glu
                165                 170                 175
Gly Ala Glu Val Lys Tyr Glu Gly His Trp Arg Gln Val Cys Asp
                180                 185                 190
Gln Gly Trp Thr Met Asn Asn Ser Arg Val Val Cys Gly Met Leu Gly
                195                 200                 205
Phe Pro Ser Glu Val Pro Val Asp Ser His Tyr Tyr Arg Lys Val Trp
                210                 215                 220
Asp Leu Lys Met Arg Asp Pro Lys Ser Arg Leu Lys Ser Leu Thr Asn
225                 230                 235                 240
Lys Asn Ser Phe Trp Ile His Gln Val Thr Cys Leu Gly Thr Glu Pro
                245                 250                 255
His Met Ala Asn Cys Gln Val Gln Val Ala Pro Ala Arg Gly Lys Leu
                260                 265                 270
Arg Pro Ala Cys Pro Gly Gly Met His Ala Val Val Ser Cys Val Ala
                275                 280                 285
Gly Pro His Phe Arg Pro Pro Lys Thr Lys Pro Gln Arg Lys Gly Ser
                290                 295                 300
Trp Ala Glu Glu Pro Arg Val Arg Leu Arg Ser Gly Ala Gln Val Gly
305                 310                 315                 320
Glu Gly Arg Val Glu Val Leu Met Asn Arg Gln Trp Gly Thr Val Cys
                325                 330                 335
Asp His Arg Trp Asn Leu Ile Ser Ala Ser Val Val Cys Arg Gln Leu
                340                 345                 350
Gly Phe Gly Ser Ala Arg Glu Ala Leu Phe Gly Ala Arg Leu Gly Gln
                355                 360                 365
Gly Leu Gly Pro Ile His Leu Ser Glu Val Arg Cys Arg Gly Tyr Glu
                370                 375                 380
Arg Thr Leu Ser Asp Cys Pro Ala Leu Glu Gly Ser Gln Asn Gly Cys
385                 390                 395                 400
Gln His Glu Asn Ala Ala Ala Val Arg Cys Asn Val Pro Asn Met Gly
                405                 410                 415
Phe Gln Asn Gln Val Arg Leu Ala Gly Gly Arg Ile Pro Glu Glu Gly
                420                 425                 430
Leu Leu Glu Val Gln Val Glu Val Asn Gly Val Pro Arg Trp Gly Ser
                435                 440                 445
Val Cys Ser Glu Asn Trp Gly Leu Thr Glu Ala Met Val Ala Cys Arg
                450                 455                 460
Gln Leu Gly Leu Gly Phe Ala Ile His Ala Tyr Lys Glu Thr Trp Phe
465                 470                 475                 480
Trp Ser Gly Thr Pro Arg Ala Gln Glu Val Val Met Ser Gly Val Arg
                485                 490                 495
Cys Ser Gly Thr Glu Leu Ala Leu Gln Gln Cys Gln Arg His Gly Pro
                500                 505                 510
```

```
Val His Cys Ser His Gly Gly Gly Arg Phe Leu Ala Gly Val Ser Cys
        515                 520                 525

Met Asp Ser Ala Pro Asp Leu Val Met Asn Ala Gln Leu Val Gln Glu
    530                 535                 540

Thr Ala Tyr Leu Glu Asp Arg Pro Leu Ser Gln Leu Tyr Cys Ala His
545                 550                 555                 560

Glu Glu Asn Cys Leu Ser Lys Ser Ala Asp His Met Asp Trp Pro Tyr
                565                 570                 575

Gly Tyr Arg Arg Leu Leu Arg Phe Ser Thr Gln Ile Tyr Asn Leu Gly
            580                 585                 590

Arg Thr Asp Phe Arg Pro Lys Thr Gly Arg Asp Ser Trp Val Trp His
        595                 600                 605

Gln Cys His Arg His Tyr His Ser Ile Glu Val Phe Thr His Tyr Asp
    610                 615                 620

Leu Leu Thr Leu Asn Gly Ser Lys Val Ala Glu Gly His Lys Ala Ser
625                 630                 635                 640

Phe Cys Leu Glu Asp Thr Asn Cys Pro Thr Gly Leu Gln Arg Arg Tyr
                645                 650                 655

Ala Cys Ala Asn Phe Gly Glu Gln Gly Val Thr Val Gly Cys Trp Asp
            660                 665                 670

Thr Tyr Arg His Asp Ile Asp Cys Gln Trp Val Asp Ile Thr Asp Val
        675                 680                 685

Gly Pro Gly Asn Tyr Ile Phe Gln Val Ile Val Asn Pro His Tyr Glu
    690                 695                 700

Val Ala Glu Ser Asp Phe Ser Asn Asn Met Leu Gln Cys Arg Cys Lys
705                 710                 715                 720

Tyr Asp Gly His Arg Val Trp Leu His Asn Cys His Thr Gly Asn Ser
                725                 730                 735

Tyr Pro Ala Asn Ala Glu Leu Ser Leu Glu Gln Glu Gln Arg Leu Arg
            740                 745                 750

Asn Asn Leu Ile
        755

<210> SEQ ID NO 3
<211> LENGTH: 103
<212> TYPE: PRT
<213> ORGANISM: Human

<400> SEQUENCE: 3

Leu Arg Leu Val Gly Pro Glu Ser Lys Pro Glu Glu Gly Arg Leu Glu
1               5                   10                  15

Val Leu His Gln Gly Gln Trp Gly Thr Val Cys Asp Asp Asn Phe Ala
            20                  25                  30

Ile Gln Glu Ala Thr Val Ala Cys Arg Gln Leu Gly Phe Glu Ala Ala
        35                  40                  45

Leu Thr Trp Ala His Ser Ala Lys Tyr Gly Gln Gly Glu Gly Pro Ile
    50                  55                  60

Trp Leu Asp Asn Val Arg Cys Val Gly Thr Glu Ser Ser Leu Asp Gln
65                  70                  75                  80

Cys Gly Ser Asn Gly Trp Gly Val Ser Asp Cys Ser His Ser Glu Asp
                85                  90                  95

Val Gly Val Ile Cys His Pro
            100
```

```
<210> SEQ ID NO 4
<211> LENGTH: 125
<212> TYPE: PRT
<213> ORGANISM: Human

<400> SEQUENCE: 4

Pro Ile Leu Ala Ser Ala Lys Gln His Ser Pro Val Thr Glu Gly Ala
 1               5                  10                  15

Val Glu Val Lys Tyr Glu Gly His Trp Arg Gln Val Cys Asp Gln Gly
                20                  25                  30

Trp Thr Met Asn Asn Ser Arg Val Val Cys Gly Met Leu Gly Phe Pro
            35                  40                  45

Ser Glu Val Pro Val Asp Ser His Tyr Tyr Arg Lys Val Trp Asp Leu
        50                  55                  60

Lys Met Arg Asp Pro Lys Ser Arg Leu Lys Ser Leu Thr Asn Lys Asn
65                  70                  75                  80

Ser Phe Trp Ile His Gln Val Thr Cys Leu Gly Thr Glu Pro His Met
                85                  90                  95

Ala Asn Cys Gln Val Gln Val Ala Pro Ala Arg Gly Lys Leu Arg Pro
            100                 105                 110

Ala Cys Pro Gly Gly Met His Ala Val Val Ser Cys Val
        115                 120                 125

<210> SEQ ID NO 5
<211> LENGTH: 101
<212> TYPE: PRT
<213> ORGANISM: Human

<400> SEQUENCE: 5

Val Arg Leu Arg Ser Gly Ala Gln Val Gly Glu Gly Arg Val Glu Val
 1               5                  10                  15

Leu Met Asn Arg Gln Trp Gly Thr Val Cys Asp His Arg Trp Asn Leu
                20                  25                  30

Ile Ser Ala Ser Val Val Cys Arg Gln Leu Gly Phe Gly Ser Ala Arg
            35                  40                  45

Glu Ala Leu Phe Gly Ala Arg Leu Gly Gln Gly Leu Gly Pro Ile His
        50                  55                  60

Leu Ser Glu Val Arg Cys Arg Gly Tyr Glu Arg Thr Leu Ser Asp Cys
65                  70                  75                  80

Pro Ala Leu Glu Gly Ser Gln Asn Gly Cys Gln His Glu Asn Ala Ala
                85                  90                  95

Ala Val Arg Cys Asn
            100

<210> SEQ ID NO 6
<211> LENGTH: 109
<212> TYPE: PRT
<213> ORGANISM: Human

<400> SEQUENCE: 6

Val Arg Leu Ala Gly Gly Arg Ile Pro Glu Glu Gly Leu Leu Glu Val
 1               5                  10                  15

Gln Val Glu Val Asn Gly Val Pro Arg Trp Gly Ser Val Cys Ser Glu
                20                  25                  30

Asn Trp Gly Leu Thr Glu Ala Met Val Ala Cys Arg Gln Leu Gly Leu
            35                  40                  45

Gly Phe Ala Ile His Ala Tyr Lys Glu Thr Trp Phe Trp Ser Gly Thr
        50                  55                  60
```

```
Pro Arg Ala Gln Glu Val Val Met Ser Gly Val Arg Cys Ser Gly Thr
 65                  70                  75                  80

Glu Leu Ala Leu Gln Gln Cys Gln Arg His Gly Pro Val His Cys Ser
                 85                  90                  95

His Gly Gly Gly Arg Phe Leu Ala Gly Val Ser Cys Met
            100                 105
```

<210> SEQ ID NO 7
<211> LENGTH: 227
<212> TYPE: PRT
<213> ORGANISM: Human

<400> SEQUENCE: 7

```
Asp Ser Ala Pro Asp Leu Val Met Asn Ala Gln Leu Val Gln Glu Thr
  1               5                  10                  15

Ala Tyr Leu Glu Asp Arg Pro Leu Ser Gln Leu Tyr Cys Ala His Glu
                 20                  25                  30

Glu Asn Cys Leu Ser Lys Ser Ala Asp His Met Asp Trp Pro Tyr Gly
             35                  40                  45

Tyr Arg Arg Leu Leu Arg Phe Ser Thr Gln Ile Tyr Asn Leu Gly Arg
 50                  55                  60

Thr Asp Phe Arg Pro Lys Thr Gly Arg Asp Ser Trp Val Trp His Gln
 65                  70                  75                  80

Cys His Arg His Tyr His Ser Ile Glu Val Phe Thr His Tyr Asp Leu
                 85                  90                  95

Leu Thr Leu Asn Gly Ser Lys Val Ala Glu Gly His Lys Ala Ser Phe
            100                 105                 110

Cys Leu Glu Asp Thr Asn Cys Pro Thr Gly Leu Gln Arg Arg Tyr Ala
        115                 120                 125

Cys Ala Asn Phe Gly Glu Gln Gly Val Thr Val Gly Cys Trp Asp Thr
130                 135                 140

Tyr Arg His Asp Ile Asp Cys Gln Trp Val Asp Ile Thr Asp Val Gly
145                 150                 155                 160

Pro Gly Asn Tyr Ile Phe Gln Val Ile Val Asn Pro His Tyr Glu Val
                165                 170                 175

Ala Glu Ser Asp Phe Ser Asn Asn Met Leu Gln Cys Arg Cys Lys Tyr
            180                 185                 190

Asp Gly His Arg Val Trp Leu His Asn Cys His Thr Gly Asn Ser Tyr
        195                 200                 205

Pro Ala Asn Ala Glu Leu Ser Leu Glu Gln Glu Gln Arg Leu Arg Asn
    210                 215                 220

Asn Leu Ile
225
```

<210> SEQ ID NO 8
<211> LENGTH: 15
<212> TYPE: DNA
<213> ORGANISM: Artificial Sequence
<220> FEATURE:
<223> OTHER INFORMATION: Oligonucleotide

<400> SEQUENCE: 8 agctttttttt ttttc                                                            15

<210> SEQ ID NO 9
<211> LENGTH: 13
<212> TYPE: DNA

```
<213> ORGANISM: Artificial Sequence
<220> FEATURE:
<223> OTHER INFORMATION: Arbitrary Primer

<400> SEQUENCE: 9
aagcttgcca tgg                                                        13

<210> SEQ ID NO 10
<211> LENGTH: 19
<212> TYPE: DNA
<213> ORGANISM: Artificial Sequence
<220> FEATURE:
<223> OTHER INFORMATION: Oligo primer

<400> SEQUENCE: 10
tttgctcagc tgagctcct                                                  19

<210> SEQ ID NO 11
<211> LENGTH: 22
<212> TYPE: DNA
<213> ORGANISM: Artificial Sequence
<220> FEATURE:
<223> OTHER INFORMATION: Oligo primer

<400> SEQUENCE: 11
taagataaag gtaaggacac ta                                              22
```

MEMBER OF THE LYSYL OXIDASE GENE FAMILY

PRIORITY

This application claims priority under 35 U.S.C. § 119 from U.S. Provisional Patent Application Ser. No. 60/223,763, filed Aug. 8, 2000 and U.S. Provisional Patent Application Ser. No. 60/255,838, filed Dec. 15, 2000; each of which is hereby incorporated by reference in its entirety.

FIELD OF THE INVENTION

The present invention relates to a novel member of the lysyl oxidase family, EER-7, polypeptide fragments of the protein, and nucleic acids encoding the EER-7 protein and fragments. The present invention also relates to an assay system and method for testing estrogen receptor-binding compounds for their ability to regulate EER-7 mRNA transcription.

BACKGROUND OF THE INVENTION

Abdominal aortic aneurysms (AAAs) are an important vascular condition in the United States and other developed nations, where a progressive increase in incidence has been observed over the past 30 years (Mitchell et al., Vascular Surgery, 4th edition, 1995, 1032–1060). The majority of AAAs affect men over the age of 55, but a steady rise in incidence has also been observed in women (Cole et al., Chronic Dis. Canada, 1994,15:S1–S64; Krupski et al. Semin. Vasc. Surg., 1995, 8:83–167).

Elastin and collagen (types I and III) are the principal structural proteins of the aorta. These fibrillar proteins impart both strength and resilience to the aortic wall during its continual exposure to the stress of pulsatile arterial pressure. Because AAAs display a decrease in elastin concentration and histopathologic changes in which the elastic lamellae are fragmented and degraded, the loss of elastin and its biophysical properties has been considered an essential feature (Campa, et al., Artherosclerosis, 1987, 65:13–21; White et al., J. Vasc. Surg., 1993, 17:371–381; Halloran, et al., J. Surg. Res., 1995, 8:85–92). The fact that most aneurysms arise in the infrarenal aorta has been attributed to the fact that aortic elastin content and the number of elastic lamellae are both normally lower in this region than in more proximal parts of the aorta. The infrarenal aorta would therefore appear to be predisposed to aneurysms induced by any process causing accelerated elastin degradation.

Lysyl oxidase (LO, E.C. 1.4.3.13) initiates covalent crosslinking between and within the molecular units of elastin and of collagen by oxidizing peptidyl lysine in these proteins to peptidyl α-aminoadipic-δ-semialdehyde. The peptidyl aldehyde can then condense with neighboring amino groups or peptidyl aldehydes to form the covalent crosslinkages found in fibrillar collagen and elastin (Kagan, Biology of the Extracellular Matrix, 1986, 321–398). LO contains one mole tightly bound copper (II) cofactor per mole of purified, 32 kDa enzyme which correlates with the maximum expression of enzyme activity. The copper cofactor is bound in a tetragonally distorted, octahedrally coordinated ligand field (Gacheru et al., J. Biol. Chem., 1990, 265:19022–19027). A full length cDNA predicted to encode a protein of 409 amino acids (46 kDa) was first identified within a neonatal rat aorta cDNA λgt11 expression library using anti-bovine lysyl oxidase antiserum. Human (Hamalainen et al., Genomics, 1991, 17:544–548; Mariani et al., Matrix, 1992, 12:242–248), chick (Wu et al., J. Biol. Chem., 1992, 267:24199–24206) and mouse (Kenyon et al., Science, 1991, 253:802) LO cDNAs have now been cloned and sequenced, revealing the presence of both conserved and divergent sequence elements among the four predicted LO protein sequences.

A human cDNA species encoding a predicted lysyl oxidase-like (LOL) protein has been cloned and mapped to chromosome 15q24-q25. The homology of this LOL gene to LO begins at the exon 1–2 boundary in the mouse LO gene (Kenyon et al., J. Biol. Chem., 1993, 268:18435–18437). More recently, a novel cDNA with a predicted protein sequence is 48% homologous to LO and LOL has been identified in senescent human fibroblasts (Saito et al., J. Biol. Chem., 1997, 272:8157–5160). The existence of this series of highly related genes implies the existence of a lysyl oxidase gene family, additional members of which may yet be identified. However, the nature and catalytic function of the expressed protein product of these genes has been documented only for that coding for the known lysyl oxidase enzyme species of connective tissues. Recent studies indicate that LO activity may be modulated by estrogen receptors (Ozasa et al., Endocrinology, 1981, 109:618–621; Sanada et al., Biochim. Biophys. Acta., 1978, 541:408–413).

SUMMARY OF THE INVENTION

The present invention provides a novel LO protein termed EER-7. Nucleic acid sequences, protein sequence, nucleic acid and protein fragments, oligonucleotides, vectors, transformed host cells, and specific EER-7 antibodies are also contemplated by the present invention. Methods of producing the EER-7 protein from transformed host cells and detecting EER-7 protein in a sample are also contemplated. In a preferred embodiment, the protein is mammalian. In a further embodiment the protein is human.

In an alternative embodiment, a polypeptide fragment of an EER-7 protein consists of one to four copies of SRCR domains, a conserved catalytic domain of lysyl oxidase, is specifically recognized with an anti-EER-7 antibody, or any combination thereof.

The present invention also provides for an assay system for identifying selective estrogen receptor ligands, where transformed cells that express different estrogen receptors are present and where the number of cells is sufficient to produce a detectable amount of EER-7 mRNA. In a preferred embodiment, the transformed cells comprise two different populations. A method of identifying selective estrogen receptor ligands using this assay system also is contemplated.

A non-human EER-7 knockout animal, where endogenous EER-7 expression is suppressed in the animal in contemplated by the present invention. Additionally, the present invention further provides for a non-human animal transformed with a vector comprising a nucleic acid encoding a protein that regulates EER-7 expression.

DETAILED DESCRIPTION OF THE INVENTION

Figure 1:
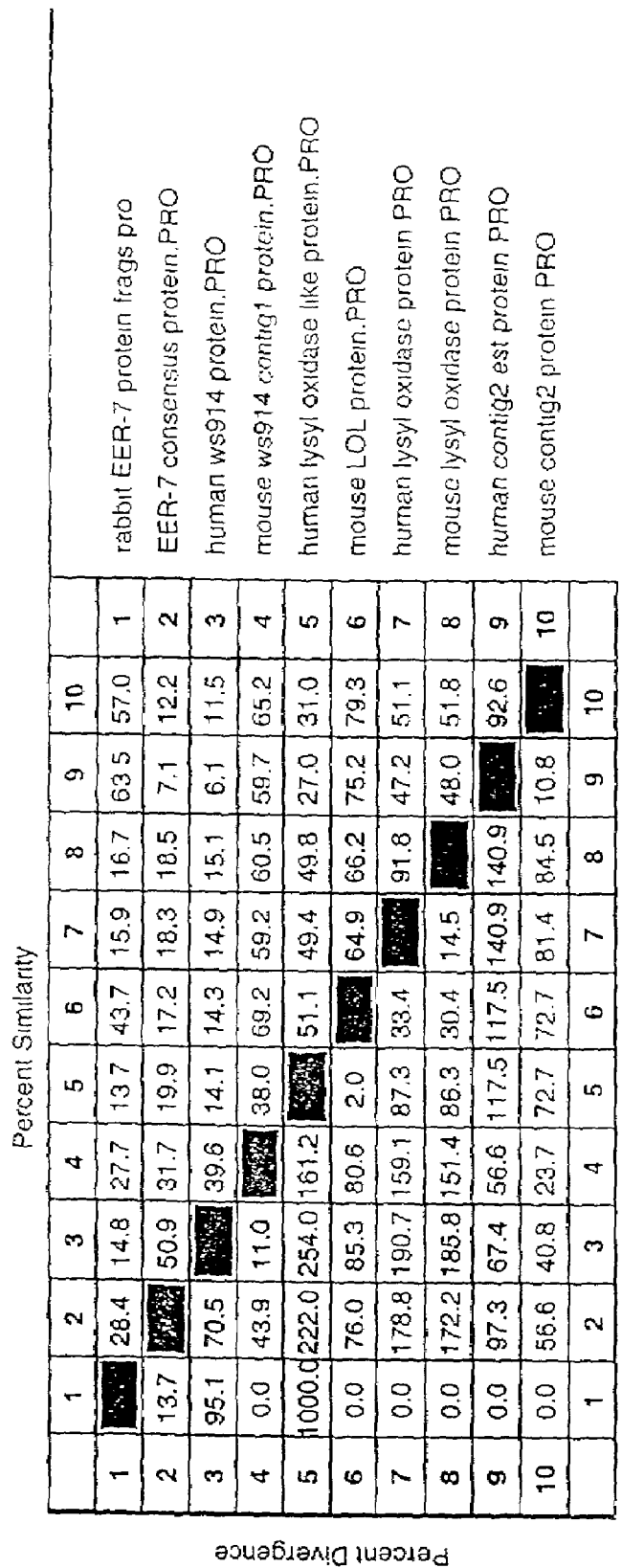
FIG. 1. Sequence pair distances of protein alignment, using Clustal method with PAM250 residue weight table, with rabbit EER-7 protein fragrnents, EER-7 consensus protein, human and mouse WS914, human and mouse LOL, human and mouse LO, and human and mouse EST.

The present invention is based, in part, on discovery of a novel cDNA (EER-7; SEQ ID NO.: 1) whose expression is regulated by estrogen. Human umbilical vein cells, HUVEC, were transformed with a human ER expression vector. Transformed cells in multi-well plates were treated with estrogen or test compounds, and EER-7 mRNA expression was determined with Northern analysis and realtime PCR. Modulation of EER-7 mRNA expression is both ER and ligand dependent. The nucleic acid sequence of EER-7 shows homology to known lysyl oxidase genes. All previously identified lysyl oxidase catalytic domains are present in the EER-7 protein. The catalytic domain of the EER-7 protein is located from about amino acid 530 to about amino acid 756. Furthermore, EER-7 contains four copies of Scavenger Receptor Cysteine Rich (SRCR) domains (named SRCR-1 to SRCR-4), which are proposed to play a role in protein-protein interactions. The amino acids defining the SRCR domains of EER-7 are SRCR-1: about 32 to about 134, SRCR-2: about 163 to about 287, SRCR-3: about 311 to about 411, and SRCR-4: about 421 to about 529. EER-7 shares sequence identity with LO, LOL, WS914 (a novel LOL protein isolated from patient's diagnosed with Warner's Syndrome) and novel EER-7 proteins from other species (e.g., rabbit). Sequence comparison indicates an overall sequence identity from about 10% to about 51%. Comparison of the SRCR domains indicates sequence similarity to WS914 from about 34% to about 64%. Human EER-7 shares about 45% sequence identity of its catalytic domain with the catalytic domains of human LO and LOL.

The present invention also advantageously provides a screening assay for identifying compounds that selectively regulate specific isoforms of the ER by evaluating the effect of test compounds on EER-7 expression. The assay system of the invention is suitable for high throughput screening, e.g., screening thousands of compounds per assay.

The present invention contemplates comparing the EER-7 responses of two cell populations transfected with different ER isoforms when they are contacted with a test compound. A difference in the response of the populations indicates that the test compounds differentially agonize or antagonize different ER isoforms. Such compounds are good leads or candidates for ER-based therapeutics, such as non-feminizing estrogen compounds.

Thus, the present invention advantageously provides EER-7 protein, including fragments, derivatives, and analogs of EER-7; EER-7 nucleic acids, including oligonucleotide primers and probes, and EER-7 regulatory sequences; EER-7-specific antibodies; and related methods of using these materials to detect the presence of EER-7 proteins or nucleic acids, EER-7 binding partners, and in screens for agonists and antagonists of EER-7. The following sections of the application, which are delineated by headings (in bold) and sub-headings (in bold italics), which cover these three aspects of the invention, are provided for clarity, and not by way of limitation.

General Definitions

As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure; and more preferably still at least 99% pure. Purity can be evaluated by chromatography, gel electrophoresis, immunoassay, composition analysis, biological assay, and other methods known in the art.

Methods for purification are well-known in the art. For example, nucleic acids can be purified by precipitation, chromatography (including preparative solid phase chromatography, oligonucleotide hybridization, and triple helix chromatography), ultracentrifagation, and other means. Polypeptides and proteins can be purified by various methods including, without limitation, preparative disc-gel electrophoresis, isoelectric focusing, HPLC, reversed-phase HPLC, gel filtration, ion exchange and partition chromatography, precipitation and salting-out chromatography, extraction, and countercurrent distribution. For some purposes, it is preferable to produce the polypeptide in a recombinant system in which the protein contains an additional sequence tag that facilitates purification, such as, but not limited to, a polyhistidine sequence, or a sequence that specifically binds to an antibody, such as FLAG and GST. The polypeptide can then be purified from a crude lysate of the host cell by chromatography on an appropriate solid-phase matrix. Alternatively, antibodies produced against the protein or against peptides derived therefrom can be used as purification reagents. Cells can be purified by various techniques, including centrifugation, matrix separation (e.g., nylon wool separation), panning and other immunoselection techniques, depletion (e.g., complement depletion of contaminating cells), and cell sorting (e.g., fluorescence activated cell sorting [FACS]). Other purification methods are possible. A purified material may contain less than about 50%, preferably less than about 75%, and most preferably less than about 90%, of the cellular components with which it was originally associated. The "substantially pure" indicates the highest degree of purity which can be achieved using conventional purification techniques known in the art.

In a specific embodiment, the term "about" or "approximately" means within a scientifically acceptable error range for a given value relative to the prescision with which the value is or can be measured, e.g., within 20%, preferably within 10%, and more preferably within 5% of a given value or range. Alternatively, particularly with biological systems, the term can mean within an order of magnitude, preferably within 5-fold, and more preferably within 2-fold of a given value.

A "sample" as used herein refers to a biological material which can be tested for the presence of EER-7 protein or EER-7 nucleic acids. Such samples can be obtained from animal subjects, such as humans and non-human animals, and include tissue, especially muscle, biopsies, blood and blood products; plural effusions; cerebrospinal fluid (CSF); ascites fluid; and cell culture.

Non-human animals include, without limitation, laboratory animals such as mice, rats, rabbits, hamsters, guinea pigs, etc.; domestic animals such as dogs and cats; and, farm animals such as sheep, goats, pigs, horses, and cows.

The use of italics indicates a nucleic acid molecule (e.g., EER-7 cDNA, gene, etc.); normal text indicates the polypeptide or protein.

The term "selective" refers to the ability of an ER ligand to elicit different responses from different ER isoforms. Stated differently, a selective ER ligand may be a potent agonist for one ER isoform, such as ERα, while agonizing another ER isoform, such as ERβ, poorly or not at all. Conversely, a compound can be a potent ERβ agonist and a poor ERα agonist. Similarly, ER ligands can differentially antagonize ER isoforms. The present invention advantageously permits dissection of those activities.

The term "ability to elicit a response" refers to the ability of an ER ligand to agonize or antagonize ER activity.

As used herein the term "transformed cell" refers to a modified host cell that expresses a functional estrogen receptor expressed from a vector encoding the estrogen receptor and that can express EER-7. Any cell can be used, preferably a mammalian cell, and more preferably an endothelial cell. In a specific embodiment, the cell is a human umbilical vein cell.

A "functional estrogen receptor" is a receptor that binds estrogen or estrogen analogs and transduces a signal upon such binding. Preferably the ER is a human ER (hER), for example ERα or ERβ. Estrogen receptors may be derived from a variety of sources, including mammal, e.g., human, bovine, porcine, and canine; and avian.

The cells of the invention are particularly suitable for an assay system for estrogen receptor ligands that modulate EER-7 mRNA expression. An "assay system" is one or more collections of such cells, e.g., in a microwell plate or some other culture system. To permit evaluation of the effects of a test compound on the cells, the number of cells in a single assay system is sufficient to express a detectable amount of the regulated EER-7 mRNA expression at least under conditions of maximum EER-7 mRNA expression.

A "test compound" is any molecule, such as an estrogen compound, that can be tested for its ability to modulate EER-7 expression through the ER, as set forth herein.

As used herein, the term "provide" refers to supplying the compounds or pharmaceutical compositions of the present invention to an animal, preferably a human, in any form. For example, a prodrug form of the compounds may be provided the subject, which then is metabolized to the compound in the body.

EER-7

EER-7 protein, as defined herein, refers to a polypeptide having about 756 amino acids. In a specific embodiment, human EER-7 has 740 amino acids. EER-7 can have a molecular weight of about 82.6 kilo-Daltons (kDa), as measured by SDS-polyacrylamide gel electrophoresis. EER-7 gene has significant homology with other LO oxidase genes. Thus, EER-7 refers to a protein having greater than about 60%, preferably greater than 80%, more preferably still greater than 90%, and even more preferably greater than 95% overall sequence identity to SEQ ID NO: 2. In a specific embodiment, EER-7 has amino acid sequence as shown in SEQ ID NO: 2. Since EER-7 contains a secretory leader sequence and no identifiable transmembrane regions, EER-7 is proposed to be a secreted protein. EER-7 is comprised of four SRCR domains and a catalytic domain. SRCR domains target proteins to specific extracellular targets.

Sequence comparison studies between human EER-7 protein and LO, LOL, WS914, and EER-7 proteins from other species, indicates values of sequence similarity ranging from 7% and 51% (see FIG. 1). Human EER-7 protein shares an overall 18% percent sequence similarity to human LO protein. Since LO does not contain the SRCR domains, comparison of only the catalytic domains of EER-7 (SEQ ID NO: 7) and LO indicates a 46% sequence similarity (See FIG. 2). The catalytic domain of EER-7 also shares 46% and 66% sequence similarity to the catalytic domains of human LOL and WS914, respectively. Comparison of the four SRCR domains in EER-7 to those present in WS914, show that sequence similarity varies between domains. SRCR domains 1, 3, and 4 (SEQ ID NOs: 3, 4 and 6) in EER-7 share about 60% sequence similarity to the same domains in WS914, while SRCR-2 (SEQ ID NO: 5) shares about 34% sequence similarity.

EER-7, like other members of the lysyl oxidase enzymes class of copper amino oxidases, initiates cross-linking between and within units of elastin and collagen. Stimulation of lysyl-oxidase enzyme activity of EER-7 can be a target for treatment of AAAs and myocardial infractions. Tropoelastin is a substrate for lysyl oxidase and increased EER-7 lysyl oxidase activity increases elastin cross-linking. Increased elastin cross-linking in the inner elastic lamina prevents development of aneurysms. Increased EER-7 lysyl oxidase activity also would increase the number of collagen cross linkings and thus increase the tensile strength of the vessel wall, which also may prevent an aneurysm. Myocardial infractions may be prevented by inhibiting the rupture of the fibrous cap that covers plaque in the coronary vessels. Increased tensile strength of the cap, resulting from increased lysyl oxidase activity, can help prevent the infarctions. Additionally, inhibition of LO activity has been implicated in treatment of fibrotic diseases.

EER-7 fragments, derivatives, and analogs can be characterized by one or more of the characteristics of EER-7 protein. For example, an EER-7 fragment, also termed herein an EER-7 peptide or polypeptide, can have an amino acid sequence corresponding to a homology region of lysyl oxidase protein, and in particular one of the fragments having SEQ ID NOs: 3–7. In a specific embodiment, in order to develop the specific C-terminal and N-terminal EER-7 antibodies, antibodies can be raised against either of the two halves of EER-7 protein, or antigenic peptides of each half.

Analogs and derivatives of EER-7 of the invention have the same or homologous characteristics of EER-7 as set forth above. For example, a truncated form of EER-7 can be provided. Such a truncated form includes EER-7 with a either an N-terminal, C-terminal, or internal deletion. In a specific embodiment, the derivative is functionally active, i.e., capable of exhibiting one or more functional activities associated with a full-length, wild-type EER-7 of the invention. Such functions include participating in formulation of covalent cross-links in collagen and/or elastin. Alternatively, an EER-7 chimeric fusion protein can be prepared in which the EER-7 portion of the fusion protein has one or more characteristics of EER-7. Such fusion proteins include fusions of EER-7 polypeptide with a marker polypeptide, such as FLAG, a histidine tag, a myc tag, or glutathione-S-transferase (GST). Alternatively, EER-7 can be fused with an expression-related peptide, such as yeast α-mating factor, a heterogeneous signal peptide, or a peptide that renders EER-7 more stable upon expression. EER-7 can also be fused with a unique phosphorylation site for labeling. In another embodiment, EER-7 can be expressed as a fusion with a bacterial protein, such as β-galactosidase.

EER-7 analogs can be made by altering encoding nucleic acid sequences by substitutions, additions or deletions that provide for functionally similar molecules, i.e., molecules that perform one or more EER-7 functions. In a specific embodiment, an analog of EER-7 is a sequence-conservative variant of EER-7. In another embodiment, an analog of EER-7 is a function-conservative variant. In yet another embodiment, an analog of EER-7 is an allelic variant or a homologous variant from another species. In a specific embodiment, human variants of EER-7 are described.

EER-7 derivatives include, but are by no means limited to, phosphorylated EER-7, myristylated EER-7, methylated EER-7, and other EER-7 proteins that are otherwise chemically modified. EER-7 derivatives also include labeled variants, e.g., radio-labeled with iodine (or, as pointed out above, phosphorous); a detectable molecule, such as but by no means limited to biotin, a chelating group complexed with a metal ion, a chromophore or fluorophore, a gold colloid, or a particle such as a latex bead; or attached to a water soluble polymer.

Chemical modification of biologically active component or components of EER-7 may provide additional advantages under certain circumstances, such as increasing the stability and circulation time of the component or components and decreasing immunogenicity (see U.S. Pat. No. 4,179,337, Davis et al., issued Dec. 18, 1979; for a review, see Abuchowski et al., in Enzymes as Drugs, J. S. Holcerberg and J. Roberts, eds. 1981, pp. 367–383). A review article describes protein modification and fusion proteins (Francis, 1992, Focus on Growth Factors 3:4–10, Mediscript: Mountview Court, Friern Barnet Lane, London N20, OLD, UK).

The chemical moieties suitable for derivatization may be selected from among water soluble polymers. The polymer selected should be water soluble so that the component to which it is attached does not precipitate in an aqueous environment, such as a physiological environment. Preferably, for therapeutic use of the end-product preparation, the polymer will be pharmaceutically acceptable. One skilled in the art will be able to select the desired polymer based on such considerations as whether the polymer/component conjugate will be used therapeutically, and if so, the desired dosage, circulation time, resistance to proteolysis, and other considerations. For the present component or components, these may be ascertained using the assays provided herein.

The water soluble polymer maybe selected from the group consisting of, for example, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols and polyvinyl alcohol. Polyethylene glycol propionaldenhyde may have advantages in manufacturing due to its stability in water. PEGylation of proteins is a well established technique to increase half-life in vivo and ensure biological activity.

Cloning and Expression of EER-7

The present invention contemplates analysis and isolation of a gene encoding a functional or mutant EER-7, including a full length, or naturally occurring form of EER-7, and any antigenic fragments thereof from any source, preferably human. It farther contemplates expression of functional or mutant EER-7 protein for evaluation, diagnosis, or therapy.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Molecular Biology—Definitions

"Amplification" of DNA as used herein denotes the use of polymerase chain reaction (PCR) to increase the concentration of a particular DNA sequence within a mixture of DNA sequences. For a description of PCR see Saiki et al., Science, 239:487, 1988.

As used herein, "sequence-specific oligonucleotides" refers to related sets of oligonucleotides that can be used to detect allelic variations or mutations in the EER-7 gene.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or anyphosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A "polynucleotide" or "nucleotide sequence" is a series of nucleotide bases (also called "nucleotides") in DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The polynucleotides herein maybe flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme. Host cells can further be used for screening or other assays, as described infra.

Proteins and enzymes are made in the host cell using instructions in DNA and RNA, according to the genetic code. Generally, a DNA sequence having instructions for a particular protein or enzyme is "transcribed" into a corresponding sequence of RNA. The RNA sequence in turn is "translated" into the sequence of amino acids which form the protein or enzyme. An "amino acid sequence" is any chain of two or more amino acids. Each amino acid is represented in DNA or RNA by one or more triplets of nucleotides. Each triplet forms a codon, corresponding to an amino acid. For example, the amino acid lysine (Lys) can be coded by the nucleotide triplet or codon AAA or by the codon AAG. (The genetic code has some redundancy, also called degeneracy, meaning that most amino acids have more than one corresponding codon.) Because the nucleotides in DNA and RNA sequences are read in groups of three for protein production, it is important to begin reading the sequence at the correct amino acid, so that the correct triplets are read. The way that a nucleotide sequence is grouped into codons is called the "reading frame."

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene", also called a "structural gene" means a DNA sequence that codes for or corresponds to a particular sequence of amino acids which comprise all or part of one or more proteins or enzymes, and may or may not include introns and regulatory DNA sequences, such as promoter sequences, 5'-untranslated region, or 3'-untranslated region which affect for example the conditions under which the gene is expressed. Some genes, which are not structural genes, may be transcribed from DNA to RNA, but are not translated into an amino acid sequence. Other genes may function as regulators of structural genes or as regulators of DNA transcription.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control of" or "operatively associated with" transcriptional and translational control sequences in a cell when RNA polymerase transcribes the coding sequence into mRNA, which is then trans-RNA spliced (if it contains introns) and translated, in the case of mRNA, into the protein encoded by the coding sequence.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a foreign nucleic acid into a cell. The term "transformation"

means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Vectors include plasmids, phages, viruses, etc.; they are discussed in greater detail below.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes.

The term "expression system" means a host cell and compatible vector under suitable conditions, e.g. for the expression of a protein coded for by foreign DNA carried by the vector and introduced to the host cell. Common expression systems include *E. coli* host cells and plasmid vectors, insect host cells and *Baculovirus* vectors, and mammalian host cells and vectors.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is such an element operatively associated with a different gene than the one it is operatively associated with in nature. In the context of the present invention, an EER-7 gene is heterologous to the vector DNA in which it is inserted for cloning or expression, and it is heterologous to a host cell containing such a vector, in which it is expressed, e.g., a HUVEC cell.

The terms "mutant" and "mutation" mean any detectable change in genetic material, e.g. DNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence. The term "variant" may also be used to indicate a modified or altered gene, DNA sequence, enzyme, cell, etc., i.e., any kind of mutant.

"Sequence-conservative variants" of a polynucleotide sequence are those in which a change of one or more nucleotides in a given codon position results in no alteration in the amino acid encoded at that position.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, maybe replaced with leucine, methionine or valine. Such changes are expected to have little or no effect on the apparent molecular weight or isoelectric point of the protein or polypeptide. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide or enzyme which has at least 60% amino acid identity as determined by BLAST or FASTA algorithms, preferably at least 75%, most preferably at least 85%, and even more preferably at least 90%, and which has the same or substantially similar properties or functions as the native or parent protein or enzyme to which it is compared.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., Cell 50:667, 1987). Such proteins (and their encoding genes) have sequence homology, as reflected by their sequence similarity, whether in terms of percent similarity or the presence of specific residues or motifs at conserved positions.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when at least about 80%, and most preferably at least about 90 or 95% of the nucleotides match over the defined length of the DNA sequences, as determined by sequence comparison algorithms, such as BLAST, FASTA, DNA Strider, etc. An example of such a sequence is an allelic or species variant of the specific EER-7 gene of the invention. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially homologous" or "substantially similar" when greater than 80% of the amino acids are identical, or greater than about 90% are similar (functionally identical). Preferably, the similar or homologous sequences are identified by alignment using, for example, the GCG (Genetics Computer Group, Program Manual for the GCG Package, Version 7, Madison, Wis.) pileup program, or any of the programs described above (BLAST, FASTA, etc.).

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS. Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC. SSC is a 0.15M NaCl, 0.015M Na-citrate solution. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–9.51). For hybridization with shorter nucleic acids, i.e., oligonucleotides, the position of mismatches becomes more important, and the length of the oligonucleotide determines its specificity (see Sambrook et al., supra, 11.7–11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2× SSC, at 42° C. in 50% formamide, 4×SSC, or under conditions that afford levels of hybridization equivalent to those observed under either of these two conditions.

As used herein, the term "oligonucleotide" refers to a nucleic acid, generally of at least 10, preferably at least 15, and more preferably at least 20 nucleotides, preferably no more than 100 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of EER-7, or to detect the presence of nucleic acids encoding EER-7. In a further embodiment, an oligonucleotide of the invention can form a triple helix with a EER-7 DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

The present invention provides antisense nucleic acids (including ribozymes), which may be used to inhibit expression of EER-7 of the invention, particularly to suppress EER-7 effects on collagen cross-linking. An "antisense nucleic acid" is a single stranded nucleic acid molecule which, on hybridizing under cytoplasmic conditions with complementary bases in an RNA or DNA molecule, inhibits the latter's role. If the RNA is a messenger RNA transcript, the antisense nucleic acid is a countertranscript or mRNA-interfering complementary nucleic acid. As presently used, "antisense" broadly includes RNA-RNA interactions, RNA-DNA interactions, ribozymes and RNase-H mediated arrest. Antisense nucleic acid molecules can be encoded by a recombinant gene for expression in a cell (e.g., U.S. Pat. No. 5,814,500; U.S. Pat. No. 5,811,234), or alternatively they can be prepared synthetically (e.g., U.S. Pat. No. 5,780,607).

Specific non-limiting examples of synthetic oligonucleotides envisioned for this invention include oligonucleotides that contain phosphorothioates, phosphotriesters, methyl phosphonates, short chain alkyl, or cycloalkyl intersugar linkages or short chain heteroatomic or heterocyclic intersugar linkages. Most preferred are those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—$PO_2$—O—$CH_2$). U.S. Pat. No. 5,677,437 describes heteroaromatic olignucleoside linkages. Nitrogen linkers or groups containing nitrogen can also be used to prepare oligonucleotide mimics (U.S. Pat. No. 5,792,844 and U.S. Pat. No. 5,783,682). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., Science 254:1497, 1991). Other synthetic oligonucleotides may contain substituted sugar moieties comprising one of the following at the 2' position: OH, SH, SCH$_3$, F, OCN, O(CH$_2$)$_n$NH$_2$ or O(CH$_2$)$_n$CH$_3$ where n is from 1 to about 10; C$_1$ to C$_{10}$ lower alkyl, substituted lower alkyl, alkaryl or aralkyl; Cl; Br; CN; CF$_3$; OCF$_3$; O—; S—, or N-alkyl; O—, S—, or N-alkenyl; SOCH$_3$; SO$_2$CH$_3$; ONO$_2$; NO$_2$; N$_3$; NH$_2$; heterocycloalkyl; heterocycloalkaryl; aminoalkylamino; polyalkylamino; substitued silyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties. Oligonucleotides may also have sugar mimetics such as cyclobutyls or other carbocyclics in place of the pentofuranosyl group. Nucleotide units having nucleosides other than adenosine, cytidine, guanosine, thymidine and uridine, such as inosine, may be used in an oligonucleotide molecule.

EER-7Nucleic Acids

A gene encoding EER-7, whether genomic DNA or cDNA, can be isolated from any source, particularly from a human cDNA or genomic library. Methods for obtaining EER-7 gene are well known in the art, as described above (see, e.g., Sambrook et al., 1989, supra). The DNA may be obtained by standard procedures known in the art from cloned DNA (e.g., a DNA "library"), and preferably is obtained from a cDNA library prepared from tissues with high level expression of the protein, by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene. Identification of the specific DNA fragment containing the desired EER-7 gene maybe accomplished in a number of ways. For example, a portion of an EER-7 gene exemplified infra can be purified and labeled to prepare a labeled probe, and the generated DNA may be screened by nucleic acid hybridization to the labeled probe (Benton and Davis, Science 196:180, 1977; Grunstein and Hogness, Proc. Natl. Acad. Sci. U.S.A. 72:3961, 1975). Those DNA fragments with substantial homology to the probe, such as an allelic variant from another individual, will hybridize. In a specific embodiment, highest stringency hybridization conditions are used to identify a homologous EER-7 gene.

Further selection can be carried out on the basis of the properties of the gene, e.g., if the gene encodes a protein product having the isoelectric, electrophoretic, amino acid composition, partial or complete amino acid sequence, antibody binding activity, or ligand binding profile of EER-7 protein as disclosed herein. Thus, the presence of the gene may be detected by assays based on the physical, chemical, immunological, or functional properties of its expressed product.

Other DNA sequences which encode substantially the same amino acid sequence as an EER-7 gene may be used in the practice of the present invention. These include but are not limited to allelic variants, species variants, sequence conservative variants, and functional variants.

Amino acid substitutions may also be introduced to substitute an amino acid with a particularly preferable property. For example, a Cys may be introduced a potential site for disulfide bridges with another Cys.

The genes encoding EER-7 derivatives and analogs of the invention can be produced by various methods known in the art. The manipulations which result in their production can occur at the gene or protein level. For example, the cloned EER-7 gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of EER-7, care should be taken to ensure that the modified gene remains within the same translational reading frame as the EER-7 gene, uninterrupted by translational stop signals, in the gene region where the desired activity is encoded.

Additionally, the EER-7-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Such modifications can be made to introduce restriction sites and facilitate cloning the EER-7 gene into an expression vector. Any technique for mutagenesis known in the art can be used, including but not limited to, in vitro site-directed mutagenesis (Hutchinson, C., et al., J. Biol. Chem. 253:6551, 1978; Zoller and Smith, DNA 3:479–488, 1984; Oliphant et al., Gene 44:177, 1986; Hutchinson et al., Proc. Natl. Acad. Sci. U.S.A. 83:710, 1986), use of TAB" linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambdaderivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired maybe produced by ligating nucleotide sequences (linkers) onto the DNA termini; these ligated linkers may comprise specific chemically synthesized oligonucleotides encoding restriction endonuclease recognition sequences. In addition, simple PCR or overlapping PCR may be used to insert a fragment into a cloning vector.

Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g.,

*E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences form the yeast 2μ plasmid.

EER-7 Regulatory Nucleic Acids

Elements of the EER-7 promoter can be identified by scanning the human genomic region upstream of the EER-7 start site, e.g., by creating deletion mutants and checking for expression, or with the TRANSFAC algorithm. Sequences up to about 6 to about 10 kilobases (kb) or more upstream from the EER-7 start site can contain tissue-specific regulatory elements.

The term "EER-7 promoter" encompasses artificial promoters. Such promoters can be prepared by deleting nonessential intervening sequences from the upstream region of the EER-7 promoter, or by joining upstream regulatory elements from the EER-7 promoter with a heterologous minimal promoter, such as the CMV immediate early promoter.

An EER-7 promoter can be operably associated with a heterogenous coding sequence, e.g., for reporter gene (luciferase and green fluorescent proteins are examples of reporter genes) in a construct. This construct will result in expression of the heterologous coding sequence under control the EER-7 promoter, e.g., a reporter gene can be expressed, under conditions that under normal conditions cause EER-7 expression. This construct can be used in screening assays, described below, for estrogen receptor agonists and antagonists.

Expression of EER-7 Polypeptides

The nucleotide sequence coding for EER-7, or antigenic fragment, derivative or analog thereof, or a functionally active derivative, including a chimeric protein, thereof, can be inserted into an appropriate expression vector, i.e., a vector which contains the necessary elements for the transcription and translation of the inserted protein-coding sequence. Thus, a nucleic acid encoding EER-7 of the invention can be operationally associated with a promoter in an expression vector of the invention. Both cDNA and genomic sequences can be cloned and expressed under control of such regulatory sequences. Such vectors can be used to express functional or functionally inactivated EER-7 polypeptides.

The necessary transcriptional and translational signals can be provided on a recombinant expression vector, or they may be supplied by the native gene encoding EER-7 and/or its flanking regions.

Potential host-vector systems include but are not limited to mammalian cell systems transfected with expression plasmids or infected with virus (e.g., vaccinia virus, adenovirus, adeno-associated virus, herpes virus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Expression of EER-7 protein may be controlled by any promoter/enhancer element known in the art, but these regulatory elements must be functional in the host selected for expression. Promoters which may be used to control EER-7 gene expression include, but are not limited to, cytomegalovirus (CMV) promoter (U.S. Pat. Nos. 5,385,839 and 5,168,062), the SV40 early promoterregion (Benoist and Chambon, 1981, Nature 290:304–310), the promoter contained in the 3' long terminal repeat of Rous sarcoma virus (Yamamoto, et al., Cell 22:787–797, 1980), the herpes thymidine kinase promoter (Wagner et al., Proc. Natl. Acad. Sci. U.S.A. 78:1441–1445, 1981), the regulatory sequences of the metallothionein gene (Brinster et al., Nature 296: 39–42, 1982); prokaryotic expression vectors such as the β-lactamase promoter (Villa-Komaroff, et al., Proc. Natl. Acad. Sci. U.S.A. 75:3727–3731, 1978), or the tac promoter (DeBoer, et al., Proc. Natl. Acad. Sci. U.S.A. 80:21–25, 1983); see also "Useful proteins from recombinant bacteria" in Scientific American, 242:74–94, 1980; promoter elements from yeast or other fungi such as the Gal 4 promoter, the ADC (alcohol dehydrogenase) promoter, PGK (phosphoglycerol kinase) promoter, alkaline phosphatase promoter; and transcriptional control regions that exhibit tissue specificity, particularly endothelial cell-specific promoters.

Alternatively, protein expression may be controlled by providing a transcriptional activator (see U.S. Pat. No. 6,015,709). The activators can be used to drive high levels of transcription from naturally-occurring, or otherwise genomically-integrated genes. The chimeric activators of the invention are particularly useful for activating transcription of integrated single copy genes, which in the past have not successfully transactivated at appreciable levels.

Soluble forms of the protein can be obtained by collecting culture fluid, or solubilizing inclusion bodies, e.g., by treatment with detergent, and if desired sonication or other mechanical processes, as described above. The solubilized or soluble protein can be isolated using various techniques, such as polyacrylamide gel electrophoresis (PAGE), isoelectric focusing, 2-dimensional gel electrophoresis, chromatography (e.g., ion exchange, affinity, immunoaffinity, and sizing column chromatography), centrifugation, differential solubility, immunoprecipitation, or by any other standard technique for the purification of proteins.

Vectors

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMa1-C2, pET, pGEX (Smith et al., Gene 67:31–40, 1988), pMB9 and their derivatives, plasmids such as RP4; phage DNAS, e.g., the numerous derivatives of phage 1, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Viral vectors, such as lentiviruses, retroviruses, herpes viruses, adenoviruses, adeno-associated viruses, vaccinia virus, alphavirus, baculovirus, and other recombinant viruses with desirable cellular tropism. Thus, a gene encoding a functional or mutant EER-7 protein or polypeptide domain fragment thereof can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in International Patent Publication WO 95/28494, published October 1995.

Viral vectors commonly used for in vivo or ex vivo targeting and therapy procedures are DNA-based vectors and retroviral vectors. Methods for constructing and using viral vectors are known in the art (see, e.g., Miller and Rosman, BioTechniques, 7:980–990, 1992). Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part) or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome which are necessary for encapsidating the viral particles.

DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Molec. Cell. Neurosci. 2:320–330, 1991), defective herpes virus vector lacking a glyco-protein L gene (Patent Publication RD 371005 A), or other defective herpes virus vectors (International Patent Publication No. WO 94/21807, published Sep. 29, 1994; International Patent Publication No. WO 92/05263, published Apr. 2, 1994); an attenuated adenovirus vector, such as the vector described by Stratford-Perricaudet et al. (J. Clin. Invest. 90:626–630, 1992; see also La Salle et al., Science 259:988–990, 1993); a defective adeno-associated virus vector (Samulski et al., J. Virol. 61:3096–3101, 1987; Samulski et al., J. Virol. 63:3822–3828, 1989; Lebkowski et al., Mol. Cell. Biol. 8:3988–3996, 1988); and a Sinbidis virus vector (PCT Publication No. WO 98/06237; U.S. Pat. No. 5,091,309).

Various companies produce viral vectors commercially, including but by no means limited to Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ(IFN-γ), or anti-CD4 antibody, can be provided to block humoral or cellular immune responses to the viral vectors (see, e.g., Wilson, Nature Medicine, 1995). In that regard, it is advantageous to employ a viral vector that is engineered to express a minimal number of antigens.

In another embodiment, the vector can be introduced in vivo by lipofection, as naked DNA, or with other transfection facilitating agents (peptides, polymers, etc.). Synthetic cationic lipids can be used to prepare liposomes for in vivo transfection of a gene encoding a marker (Felgner, et. al., Proc. Natl. Acad. Sci. U.S.A. 84:7413–7417, 1987; Felgner and Ringold, Science 337:387–388, 1989; see Mackey, et al., Proc. Natl. Acad. Sci. U.S.A. 85:8027–8031, 1988; Ulmer, et al., Science 259:1745–1748, 1993). Useful lipid compounds and compositions for transfer of nucleic acids are described in International Patent Publications WO 95/18863 and WO 96/17823, and in U.S. Pat. No. 5,459,127. Lipids may be chemically coupled to other molecules for the purpose of targeting (see Mackey, et al., supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., International Patent Publication WO 95/21931), peptides derived from DNA binding proteins (e.g., International Patent Publication WO 96/25508), or a cationic polymer (e.g., International Patent Publication WO95/21931).

Alternatively, non-viral DNA vectors for gene therapy can be introduced into the desired host cells by methods known in the art, e.g., electroporation, microinjection, cell fusion, DEAE dextran, calcium phosphate precipitation, use of a gene gun (ballistic transfection; see, e.g., U.S. Pat. No. 5,204,253, U.S. Pat. No. 5,853,663, U.S. Pat. No. 5,885,795, and U.S. Pat. No. 5,702,384 and see Sanford, TIB-TECH, 6:299–302, 1988; Fynan et al., Proc. Natl. Acad. Sci. U.S.A., 90:11478–11482, 1993; and Yang et al, Proc. Natl. Acad. Sci. U.S.A., 87:1568–9572, 1990), or use of a DNA vector transporter (see, e.g., Wu, et al., J. Biol. Chem. 267:963–967, 1992; Wu and Wu, J. Biol. Chem. 263: 14621–14624, 1988; Hartmut, et al., Canadian Patent Application No. 2,012,311, filed Mar. 15, 1990; Williams, et al., Proc. Natl. Acad. Sci. USA 88:2726–2730, 1991). Receptor-mediated DNA delivery approaches can also be used (Curiel, et al., Hum. Gene Ther. 3:147–154, 1992; Wu and Wu, J. Biol. Chem. 262:4429–4432, 1987). U.S. Pat. Nos. 5,580, 859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Mir, et al., C.P. Acad. Sci., 321:893, 1998; WO 99/01157; WO 99/01158; WO 99/01175).

EER-7 Binding Partners and Substrates

The present invention further permits identification of physiological binding partners and substrates of EER-7. The presence of the four SRCR domains strongly indicates that EER-7 is targeted by protein-protein interactions. One method for evaluating and identifying EER-7 binding partners is the yeast two-hybrid screen. Preferably, the yeast two-hybrid screen is performed using an endothelial cell library with yeast that are transformed with recombinant EER-7. Alternatively, EER-7 can be used as a capture or affinity purification reagent. In another alternative, labeled EER-7 can be used as a probe for binding, e.g., by immunoprecipitation or Western analysis.

Generally, binding interactions between EER-7 and any of its binding partners or substrates will be strongest under conditions approximating those found in the extracellular matrix, i.e., physiological conditions of ionic strength, pH and temperature. Perturbation of these conditions will tend to disrupt the stability of a binding interaction.

Substrate candidates include, but are by no means limited to, collagen, elastin, and other extracellular matrix proteins.

Antibodies to EER-7

Antibodies to EER-7 are useful, inter alia, for diagnostics and intracellular regulation of EER-7 activity, as set forth below. According to the invention, a EER-7 polypeptide produced recombinantly or by chemical synthesis, and fragments or other derivatives or analogs thereof, including fusion proteins, may be used as an immunogen to generate antibodies that recognize the EER-7 polypeptide. Such antibodies include but are not limited to polyclonal, monoclonal, chimeric, single chain, Fab fragments, and an Fab expression library. Such an antibody is preferably specific for human EER-7 and it may recognize either a mutant form of EER-7 or wild-type EER-7, or both.

One can use the hydropathic index of amino acids, as discussed by Kyte and Doolittle (1982), wherein it was determined that certain amino acids maybe substituted for other amino acids having similar hydropathic indices and still retain a similar biological activity; to determine epitope regions. Substitution of like amino acids may be made on the basis of hydrophilicity, particularly where the biological function desired in the polypeptide to be generated is intended for use in immunological embodiments. See, for example, U.S. Pat. No. 4,554,101, which states that the greatest local average hydrophilicity of a "protein," as governed by the hydrophilicity of its adjacent amino acids, correlates with its immunogenicity. Accordingly, it is noted that substitutions can be made based on the hydrophilicity assigned to each amino acid. In using either the hydrophilicity index or hydropathic index, which assigns values to each amino acid, it is preferred to introduce substitutions of amino acids where these values are ±2, with ±1 being particularly preferred, and those within ±0.5 being the most preferred substitutions.

Various procedures known in the art may be used for the production of polyclonal antibodies to EER-7 polypeptide or derivative or analog thereof. For the production of antibody, various host animals can be immunized by injection with the EER-7 polypeptide, or a derivative (e.g., fragment or fusion protein) thereof, including but not limited to rabbits, mice, rats, sheep, goats, etc. In one embodiment, the EER-7 polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the EER-7 polypeptide, or fragment, analog, or derivative thereof, any technique that provides for the production of antibody molecules by continuous cell lines in culture may be used. These include but are not limited to the hybridoma technique originally developed by Kohler and Milstein (Nature, 1975, 256:495–497), as well as the trioma technique, the human B-cell hybridoma technique (Kozbor et al., Immunology Today 1983,4:72; Cote et al., Proc. Natl. Acad. Sci. 1983, 80:2026–2030), and the EBV-hybridoma technique to produce human monoclonal antibodies (Cole et al., in Monoclonal Antibodies and Cancer Therapy, Alan R. Liss, Inc., 1985, pp. 77–96). In an additional embodiment of the invention, monoclonal antibodies can be produced in germ-free animals (International Patent Publication No. WO 89/12690). In fact, according to the invention, techniques developed for the production of "chimeric antibodies" (Morrison et al., J. Bacteriol., 1984, 159:870); Neuberger et al., Nature, 1984, 312:604–608; Takeda et al., Nature, 1985, 314:452–454) by splicing the genes from a mouse antibody molecule specific for an EER-7 polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

According to the invention, techniques described for the production of single chain antibodies (U.S. Pat. Nos. 5,476, 786, 5,132,405, and U.S. Pat. No. 4,946,778) can be adapted to produce EER-7 polypeptide-specific single chain antibodies. An additional embodiment of the invention utilizes the techniques described for the construction of Fab expression libraries (Huse et al., Science, 1989, 246:1275–1281) to allow rapid and easy identification of monoclonal Fab fragments with the desired specificity for an EER-7 polypeptide, or its derivatives, or analogs.

In the production and use of antibodies, screening for or testing with the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an EER-7 polypeptide, one may assay generated hybridomas for a product which binds to an EER-7 polypeptide fragment containing such epitope. For selection of an antibody specific to an EER-7 polypeptide from a particular species of animal, one can select on the basis of positive binding with EER-7 polypeptide expressed by or isolated from cells of that species of animal.

The foregoing antibodies can be used in methods known in the art relating to the localization and activity of the EER-7 polypeptide, e.g., for Western blotting, imaging EER-7 polypeptide in situ, measuring levels thereof in appropriate physiological samples, etc. using any of the detection techniques mentioned above or known in the art. Such antibodies can also be used in assays for ligand binding, e.g., as described in U.S. Pat. No. 5,679,582. Antibody binding generally occurs most readily under physiological conditions, e.g., pH of between about 7 and 8, and physiological ionic strength. The presence of a carrier protein in the buffer solutions stabilizes the assays. While there is some tolerance of perturbation of optimal conditions, e.g., increasing or decreasing ionic strength, temperature, or pH, or adding detergents or chaotropic salts, such perturbations will decrease binding stability.

In a specific embodiment, antibodies that agonize or antagonize the activity of EER-7 polypeptide can be generated. In particular, intracellular single chain Fv antibodies can be used to regulate (inhibit) EER-7 (Marasco et al., Proc. Natl. Acad. Sci. U.S.A. 1993,90:7884–7893; Chen., Mol. Med. Today 1997, 3:160–167; Spitz et al., Anticancer Res. 1996, 16:3415–22; Indolfi et al., Nat. Med. 1996,2:634–635; Kijma et al., Pharmacol. Ther. 1995, 68:247–267). Such antibodies can be tested using the assays described infra for identifying ligands.

Screening and Chemistry

According to the present invention, nucleotide sequences derived from the gene encoding EER-7, and peptide sequences derived from EER-7, are useful targets to identify drugs that are effective in treating disorders associated with estrogen-regulated processes. Drug targets include without limitation (i) isolated nucleic acids derived from the gene encoding EER-7; (ii) isolated peptides and polypeptides derived from EER-7 polypeptides; and, most importantly, (iii) different estrogen receptors that selectively regulate EER-7 expression.

In particular, identification and isolation of EER-7 provides for development of screening assays, particularly for high throughput screening of molecules that up- or down-regulate the activity of EER-7, e.g., by permitting expression of EER-7 in quantities greater than can be isolated from natural sources, or in indicator cells that are specially engineered to indicate the activity of EER-7 expressed after transfection or transformation of the cells. Accordingly, the present invention contemplates methods for identifying specific estrogen receptor ligands that alter EER-7 expression, as well as molecules that act directly on EER-7, using various screening assays known in the art.

Any screening technique known in the art can be used to screen for EER-7 agonists or antagonists. The present invention contemplates screens for small molecule ligands or ligand analogs and mimics, as well as screens for natural ligands that bind to and agonize or antagonize EER-7 expression activity in vivo. For example, natural products libraries can be screened using assays of the invention for molecules that agonize or antagonize EER-7 expression or activity.

Another approach uses recombinant bacteriophage to produce large libraries. Using the "phage method" (Scott and Smith, Science 1990, 249:386–390; Cwirla, et al., Proc. Natl. Acad. Sci., USA 1990, 87:6378–6382; Devlin et al., Science 1990, 49:404–406), very large libraries can be constructed ($10^{6-108}$ chemical entities). A second approach uses primarily chemical methods, of which the Geysen method (Geysen et al., Molecular Immunology 1986, 23:709–715; Geysen et al. J. Immunologic Method 1987 102:259–274; and the method of Fodor et al. (Science 1991,251:767–773) are examples. Furka et al. (14th International Congress of Biochemistry, Volume #5 1988, Abstract FR:013; Furka, Int. J. Peptide Protein Res. 1991, 37:487–493), Houghton (U.S. Pat. No. 4,631,211) and Rutter (U.S. Pat. No. 5,010,175) describe methods to produce a mixture of peptides that can be tested as agonists or antagonists.

In another aspect, synthetic libraries (Needels et al., Proc. Natl. Acad. Sci. USA 1993, 90:10700–4; Ohlmeyer et al., Proc. Natl. Acad. Sci. USA 1993, 90:10922–10926; Lam et al., PCT Publication No. WO 92/00252; Kocis et al., PCT Publication No. WO 9428028) and the like can be used to screen for ligands that regulate EER-7 according to the present invention. Test compounds are screened from large libraries of synthetic or natural compounds. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (NC), or are readily producible. Additionally, natural and synthetically produced libraries and compounds are readily modified through conventional chemical, physical, and biochemical means (Blondelle et al., Tib Tech 1996, 14:60).

Knowledge of the primary sequence of EER-7, and the similarity of that sequence with proteins of known function, can provide an initial clue as the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

In Vivo Screening Methods

Intact cells or whole animals expressing a gene encoding EER-7 can be used in screening methods to identify candidate drugs.

In one series of embodiments, a permanent cell line is established. Alternatively, cells (including without limitation mammalian, insect, yeast, or bacterial cells) are transiently programmed to express an EER-7 gene by introduction of appropriate DNA or mRNA. Identification of candidate compounds can be achieved using any suitable assay, including without limitation (i) assays that measure selective binding of test compounds to EER-7 (ii) assays that measure the ability of a test compound to modify (i.e., inhibit or enhance) a measurable activity or function of EER-7 and (iii) assays that measure the ability of a compound to modify (i.e., inhibit or enhance) the transcriptional activity of sequences derived from the promoter (i.e., regulatory) regions of the EER-7 gene.

Transgenic mammals can be prepared for evaluating the molecular mechanisms of EER-7, and particularly human EER-7-induced signaling. Such mammals provide excellent models for screening or testing drug candidates. Thus, human protein EER-7 "knock-in" mammals can be prepared for evaluating the molecular biology of this system in greater detail than is possible with human subjects. It is also possible to evaluate compounds or diseases on "knockout" animals, e.g., to identify a compound that can compensate for a defect in EER-7 activity. Both technologies permit manipulation of single units of genetic information in their natural position in a cell genome and to examine the results of that manipulation in the background of a terminally differentiated organism. Trangenic mammals can be prepared by any method, including but not limited to modification of embryonic stem (ES) cells and heteronuclear injecion into blast cells.

A "knock-in" mammal is a mammal in which an endogenous gene is substituted with a heterologous gene (Roemer et al., New Biol. 1991, 3:331). Preferably, the heterologous gene is "knocked-in" to a locus of interest, either the subject of evaluation(in which case the gene may be a reporter gene; see Elefanty et al., Proc Natl Acad Sci USA 1998, 95:11897) of expression or function of a homologous gene, thereby linking the heterologous gene expression to transcription from the appropriate promoter. This can be achieved by homologous recombination, transposon (Westphal and Leder, Curr Biol 1997,7:530), using mutant recombination sites (Araki et al., Nucleic Acids Res 1997, 25:868) or PCR (Zhang and Henderson, Biotechniques 1998, 25:784).

EER-7 knockout mammals can be prepared for evaluating the molecular pathology of this defect in greater detail than is possible with human subjects. Such animals also provide excellent models for screening drug candidates. A "knockout mammal" is a mammal (e.g., mouse, rabbit) that contains within its genome a specific gene that has been inactivated. Any method known in the art that may render the gene non-functional or not expressed may be used. A non-limiting example of such a method is gene targeting (see, e.g., U.S. Pat. Nos. 5,777,195 and 5,616,491). A knockout mammal includes both a heterozygote knockout (i.e., one defective allele and one wild-type allele) and a homozygous mutant (i.e., two defective alleles; a heterologous construct for expression of an EER-7, such as a human EER-7, could be inserted to permit the knockout mammal to live if the lack of EER-7 expression is lethal). Preparation of a knockout mammal requires first introducing a nucleic acid construct that will be used to suppress expression of a particular gene into an undifferentiated cell type termed an embryonic stem cell. This cell is then injected into a mammalian embryo. A mammalian embryo with an integrated cell is then implanted into a foster mother for the duration of gestation. Zhou, et al. (Genes and Development 1995, 9:2623–34) describes PPCA knock-out mice.

The term "knockout" refers to partial or complete suppression of the expression of at least a portion of a protein encoded by an endogenous DNA sequence in a cell. The term "knockout construct" refers to a nucleic acid sequence that is designed to decrease or suppress expression of a protein encoded by endogenous DNA sequences in a cell. The nucleic acid sequence used as the knockout construct is typically comprised of (1) DNA from some portion of the gene (exon sequence, intron sequence, and/or promoter sequence) to be suppressed and (2) a marker sequence used to detect the presence of the knockout construct in the cell. The knockout construct is inserted into a cell, and integrates with the genomic DNA of the cell in such a position so as to prevent or interrupt transcription of the native DNA sequence. Such insertion usually occurs by homologous recombination (i.e., regions of the knockout construct that are homologous to endogenous DNA sequences hybridize to each other when the knockout construct is inserted into the cell and recombine so that the knockout construct is incorporated into the corresponding position of the endogenous DNA). The knockout construct nucleic acid sequence may comprise (1) a full or partial sequence of one or more exons and/or introns of the gene to be suppressed, (2) a full or partial promoter sequence of the gene to be suppressed, or (3) combinations thereof. Typically, the knockout construct is inserted into an embryonic stem cell (ES cell) and is integrated into the ES cell genomic DNA, usually by the process of homologous recombination. This ES cell is then injected into, and integrates with, the developing embryo.

The phrases "disruption of the gene" and "gene disruption" refer to insertion of a nucleic acid sequence into one region of the native DNA sequence (usually one or more exons) and/or the promoter region of a gene so as to decrease or prevent expression of that gene in the cell as compared to the wild-type or naturally occurring sequence of the gene. By way of example, a nucleic acid construct can be prepared containing a DNA sequence encoding an antibiotic resistance gene which is inserted into the DNA sequence that is complementary to the DNA sequence (promoter and/or coding region) to be disrupted. When this nucleic acid construct is then transfected into a cell, the construct will integrate into the genomic DNA. Thus, many progeny of the cell will no longer express the gene at least in some cells, or will express it at a decreased level, as the DNA is now disrupted by the antibiotic resistance gene.

Generally, the DNA will be at least about 1 kb in length and preferably 3–4 kb in length, thereby providing sufficient complementary sequence for recombination when the knockout construct is introduced into the genomic DNA of the ES cell (discussed below).

Included within the scope of this invention is a mammal in which two or more genes have been knocked out. Such mammals can be generated by repeating the procedures set forth herein for generating each knockout construct, or by breeding to mammals, each with a single gene knocked out, to each other, and screening for those with the double knockout genotype.

Regulated knockout animals can be prepared using various systems, such as the tet-repressor system (see U.S. Pat. No. 5,654,168) or the Cre-Lox system (see U.S. Pat. Nos. 4,959,317 and 5,801,030).

In another series of embodiments, transgenic animals are created in which (i) a human EER-7 is stably inserted into the genome of the transgenic animal; and/or (ii) the endogenous EER-7 genes are inactivated and replaced with human EER-7 genes. See, e.g., Coffman, Semin. Nephrol. 1997, 17:404; Esther et al., Lab. Invest. 1996, 74:953; Murakami et al., Blood Press. Suppl. 1996, 2:36.

In another embodiment, sequences that modulate endogenous EER-7 expression are stably inserted into the genome of the animal. For example, sequences that stimulate EER-7 expression (such as transcription factors) or that interact with and inhibit downregulatory factors may be used.

ER Activation Assay

Any cell assay system that allows for assessment of differential and/or selective functional activity of estrogen receptor isoform agonists and antagonists is defined by the present invention. In a specific embodiment, exemplified infra, the assay can be used to identify compounds that differentially interact with specific isoforms of the ER, which can be evaluated by assessing the effects of estrogen ligands cells contacted with a test compound, which modulates EER-7 mRNA transcription. The assay system can thus be used to identify compounds that selectively produce a functional effect through one estrogen receptor. Compounds that increase EER-7 mRNA transcription may result in increased EER-7 protein production and may be useful as novel therapeutics in the prevention of abdominal aortic aneurysms and myocardial infarctions. In a preferred embodiment, the assay system is comprised of two different populations of cells that express different estrogen receptors. Preferably, each experiment is performed in triplicate at multiple different dilutions of compound.

An antagonist screen involves detecting expression of the reporter gene by the host cell when contacted with an EER-7 regulatory estrogen. If EER-7 expression is decreased, the test compound is a candidate antagonist of nuclear hormone receptor signaling. If there is no change in expression of the reporter gene, the test compound is not an effective ER ligand.

The assay system described may be used to compare effects of a test compound through different estrogen receptors. Test compound effects on EER-7 transcription in different populations of transformed cells, that express different estrogen receptors, are compared to evaluate if the compounds belong to the class of estrogen receptor agonists/antagonists (see below).

Any convenient method permits detection of the expressed product. For example, the invention provides Northern blot analysis for detecting EER-7 mRNA product. The methods comprise the steps of fractionating total cellular RNA on an agarose gel, transferring RNA to a solid support membrane, and detecting a DNA-RNA complex with a labeled DNA probe, wherein the DNA probe is specific for a particular nucleic acid sequence of EER-7 under conditions in which a stable complex can form between the DNA probe and RNA components in the sample. Such complexes may be detected by using any suitable means known in the art, wherein the detection of a complex indicates the presence of EER-7 in the sample. Alternative a reporter gene under control of EER-7 expression control elements can be used in an ER activity assay.

Typically, immunoassays use either a labeled antibody or a labeled antigenic component (e.g., that competes with the antigen in the sample for binding to the antibody). Suitable labels include without limitation enzyme-based, fluorescent, chemiluminescent, radioactive, or dye molecules. Assays that amplify the signals from the probe are also known, such as, for example, those that utilize biotin and avidin, and enzyme-labelled immunoassays, such as ELISA assays.

The assay system described here also may be used in a high-throughput primary screen for agonists and antagonists, or it maybe used as a secondary functional screen for candidate compounds identified by a different primary screen, e.g., a binding assay screen that identifies compounds that interact with the receptor and affect EER-7 transcription.

Estrogen Compounds

An "estrogen compound" is defined as any of the structures described in the 11th edition of "Steroids" from Steraloids Inc., Wilton N. H., here incorporated by reference. Included in this definition are non-steroidal estrogens described in the aforementioned reference. Other estrogen compounds included in this definition are estrogen derivatives, estrogen metabolites, and estrogen precursors. Estrogen selective receptor agonists antagonists (ESRAAs) are estrogen compounds that function as agonists at ERα receptors and antagonists at ERβ receptors. Estrogen compounds that are agonists at ERβ receptors and antagonists at ERα receptors also may be identified with this assay system. The term also encompasses molecules that specifically trigger the estrogen effect described herein of regulating EER-7 transcription. Also included are mixtures of more than one estrogen or estrogen compound. Examples of such mixtures are provided in Table II of U.S. Pat. No. 5,554,601 (see column 6). Examples of estrogens having utility either alone or in combination with other agents are provided, e.g., in U.S. Pat. No. 5,554,601.

β-estrogen is the β-isomer of estrogen compounds. α-estrogen is the α-isomer of estrogen components. The term "estradiol" is either α- or β-estradiol unless specifically identified.

The term "E2" is synonymous with β-estradiol, 17β-estradiol, and β-E2. αE2 and α-estradiol is the a isomer of βE2 estradiol.

Preferably, a non-feminizing estrogen compound is used. Such a compound has the advantage of not causing uterine hypertrophy and other undesirable side effects, and thus, can be used at a higher effective dosage. Examples of non-feminizing estrogen include Raloxifene (Evista; Eli Lilly), Tamoxifen (Nolvadex; Astra Zeneca), and other selective estrogen receptor modulators.

In addition, certain compounds, such as the androgen testosterone, can be converted to estrogens in vivo by conversion with the aromatase enzyme. The aromatase enzyme is present in several regions including, but not limited to, the brain. Some androgens are substrates for aromatase and can be converted and some can not be a substrate. Those androgens that are substrates for aromatase are termed aromatizable androgens and those that are not substrates for aromatase are termed non-aromatizable androgens. Testosterone is, for example, an aromatizable androgen and dihydrotestosterone is, for example, a non-aromatizable androgen. Thus, the invention clearly extends to those compounds (and, as described infra, to using as test animals, animals in which the testes are removed or inactivated) that are converted from an androgen to an estrogen and that produces the effect described herein of decreasing the level of amyloid in vivo

High-Throughput Screen

Agents according to the invention may be identified by screening in high-throughput assays, including without limitation cell-based or cell-free assays. It will be appreciated by those skilled in the art that different types of assays can be used to detect different types of agents. Several methods of automated assays have been developed in recent years so as to permit screening of tens of thousands of compounds in a short period of time. Such high-throughput screening methods are particularly preferred. The use of high-throughput screening assays to test for agents is greatly facilitated by the availability of large amounts of purified polypeptides, as provided by the invention.

Methods of Diagnosis

According to the present invention, genetic variants of EER-7 can be detected to diagnose an EER-7 associated disease, such as increased susceptibility to abdominal aortic aneurism or myocardial infarction. The various methods for detecting such variants are described herein. Where such variants impact EER-7 function, either as a result of a mutated amino acid sequence or because the mutation results in expression of a truncated protein, or no expression at all, they are expected to result in disregulation of collagen and elastin cross-linking.

Nucleic Acid Assays

The DNA may be obtained from any cell source. DNA is extracted from the cell source or body fluid using any of the numerous methods that are standard in the art. It will be understood that the particular method used to extract DNA will depend on the nature of the source. Generally, the minimum amount of DNA to be extracted for use in the present invention is about 25 pg (corresponding to about 5 cell equivalents of a genome size of $4\times10^9$ base pairs).

In another alternate embodiment, RNA is isolated from biopsy tissue using standard methods well known to those of ordinary skill in the art such as guanidium thiocyanate-phenol-chloroform extraction (Chomocyznski et al., Anal. Biochem., 162:156, 1987). The isolated RNA is then subjected to coupled reverse transcription and amplification by polymerase chain reaction (RT-PCR), using specific oligonucleotide primers that are specific for a selected site. Conditions for primer annealing are chosen to ensure specific reverse transcription and amplification; thus, the appearance of an amplification product is diagnostic of the presence of a particular genetic variation. In another embodiment, RNA is reverse-transcribed and amplified, after which the amplified sequences are identified by, e.g., direct sequencing. In still another embodiment, cDNA obtained from the RNA can be cloned and sequenced to identify a mutation.

Protein Assays

In an alternate embodiment, biopsy tissue is obtained from a subject. Antibodies that are capable of specifically binding to EER-7 are then contacted with samples of the tissue to determine the presence or absence of a EER-7 polypeptide specified by the antibody. The antibodies may be polyclonal or monoclonal, preferably monoclonal. Measurement of specific antibody binding to cells may be accomplished by any known method, e.g., quantitative flow cytometry, enzyme-linked or fluorescence-linked immunoassay, Western analysis, etc.

Therapeutic Uses

According to the present invention, stimulation of EER-7 protein expression may be used as a treatment option in patients with estrogen-related disease states. Stimulation of EER-7 protein expression may be stimulated by methods, such as, but not limited to, (i) providing nucleic acids that encode the EER-7 protein and (ii) providing compounds that stimulate transcription and/or translation of EER-7 gene.

Gene Therapy

In a specific embodiment, vectors comprising a sequence encoding a protein, including, but not limited to, full-length EER-7, are provided to treat or prevent a disease or disorder associated with the function of EER-7 in cardiovascular functions. In this embodiment of the invention, the therapeutic vector encodes a sequence that produces the protein of the invention.

Any of the methods for gene therapy available in the art can be used according to the present invention. Exemplary methods are described below.

For general reviews of the methods of gene therapy, see, Goldspiel et al., Clinical Pharmacy, 1993, 12:488–505; Wu and Wu, Biotherapy, 1991, 3:87–95; Tolstoshev, Ann. Rev. Pharmacol. Toxicol., 1993, 32:573–596; Mulligan, Science, 1993, 260:926–932; and Morgan and Anderson, Ann. Rev. Biochem., 1993, 62:191–217; May, TIBTECH, 1993, 11:155–215. Methods commonly known in the art of recombinant DNA technology that can be used are described in Ausubel et al., (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al., (eds.), 1994, Current Protocols in Human Genetics, John Wiley & Sons, NY. Vectors suitable for gene therapy are described above.

In one aspect, the therapeutic vector comprises a nucleic acid that expresses a protein of the invention in a suitable host. In particular, such a vector has a promoter operationally linked to the coding sequence for the protein. The promoter can be inducible or constitutive and, optionally, tissue-specific. In another embodiment, a nucleic acid molecule is used in which the protein coding sequences and any other desired sequences are flanked by regions that promote homologous recombination at a desired site in the genome, thus providing for intrachromosomal expression of the protein (Koller and Smithies, Proc. Natl. Acad. Sci. U.S.A, 1989, 86:8932–8935; Zijlstra et al., Nature, 1989, 342: 435–438).

Delivery of the vector into a patient may be either direct, in which case the patient is directly exposed to the vector or a delivery complex, or indirect, in which case, cells are first transformed with the vector in vitro then transplanted into the patient. These two approaches are known, respectively, as in vivo and ex vivo gene therapy.

In a specific embodiment, the vector is directly provided in vivo, where it enters the cells of the organism and mediates expression of the protein. This can be accomplished by any of numerous methods known in the art, by constructing it as part of an appropriate expression vector and administering it so that it becomes intracellular, e.g., by infection using a defective or attenuated retroviral or other viral vector (see, U.S. Pat. No. 4,980,286), or by direct injection of naked DNA, or by use of microparticle bombardment (e.g., a gene gun; Biolistic, Dupont); or coating with lipids or cell-surface receptors or transfecting agents, encapsulation in biopolymers (e.g., poly-S-1-64-N-acetyl-glucosamine polysaccharide; see, U.S. Pat. No. 5,635,493), encapsulation in liposomes, microparticles, or microcapsules; by administering it in linkage to a peptide or other ligand known to enter the nucleus; or by administering it in linkage to a ligand subject to receptor-mediated endocytosis (see, e.g., Wu and Wu, J. Biol. Chem., 1987, 62:4429–4432), etc. In another embodiment, a nucleic acid ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publication Nos. WO 92/06180, WO 92/22635, WO 92/20316 and WO 93/14188). Alternatively, the nucleic acid can be introduced intracellularly and incorporated within host cell DNA for expression by homologous recombination (Koller and Smithies, Proc. Natl. Acad. Sci. USA, 1989, 86:8932–8935; Zijlstra, et al., Nature, 1989, 342: 435–438). These methods are in addition to those discussed above in conjunction with "Viral and Non-viral Vectors".

Alternatively, antibody molecules can also be administered, for example, by expressing nucleotide sequences encoding single-chain antibodies within the target cell population by utilizing, for example, techniques such as those described in Marasco et al. (Proc. Natl. Acad Sci. USA, 1993, 90:7889–7893).

The form and amount of therapeutic nucleic acid envisioned for use depends on the type of disease and the severity of the desired effect, patient state, etc., and can be determined by one skilled in the art.

Stimulation of Protein Synthesis

Gene transcription and protein translation may be inhibited or stimulated by administration of exogenous compounds. Exogenous compounds may interact with extracellular and/or intracellular messenger systems, such as, but not limited to, adenosine triphosphate, nitric oxide, and guanosine triphosphate; to regulate protein synthesis. In this embodiment, exogenous compounds that stimulate EER-7 protein synthesis may be used in the prevention and/or treatment of cardiovascular disorders including myocardial infarctions and aortic aneurysms. In a specific embodiment, the exogenous compound that stimulates EER-7 protein expression is an estrogen receptor ligand.

Therapeutically suggested compounds may be provided to the patient in formulations that are known in the art and may include any pharmaceutically acceptable additives, such as excipients, lubricants, diluents, flavorants, colorants, and disintegrants. The formulations may be produced in useful dosage units such as tablet, caplet, capsule, liquid, or injection.

The form and amount of therapeutic compound envisioned for use depends on the type of disease and the severity of the desired effect, patient state, etc., and can be determined by one skilled in the art.

EXAMPLES

The present invention will be better understood by reference to the following Examples, which are provided by way of exemplification and not by way of limitation.

Example 1

Discovery of EER-7

EER-7 was identified by differential display using human umbilical vein endothelial cell (HUVEC) RNA. On day 0, HUVEC were plated in maintenance media (EBM from Clonetics (San Diego, Calif.) supplemented with 10 pg/ml human EGF, 1 µg/ml hydrocortisone, 50 µg/ml gentamicin, 50 ng/ml amphotericin-B, 3 ug/ml bovine brain extract, and 2% (v/v) fetal bovine serum) at about $3 \times 10^6$ cells per 150 mm² plate. On day 1, the cells were fed phenol red-free EBM supplemented with 2% (v/v) charcoal/dextran treated fetal bovine serum (HyClone; Logan, Utah) and containing replication-defective adenovirus expressing human ERβ (Ad5ERβ) at an approximate MOI of 300. After incubation at 37° C. for 1 hour, the cells were washed twice and refed EBM/BSA (EBM supplemented with 0.25% (w/v) bovine serum albumin, 10 U/ml penicillin G, 10 ug/ml streptomycin, and 25 ng/ml amphotericin B). After approximately 6 hours additional incubation at 37° C., the cells were refed EBM/BSA containing either 100 nM 17β-estradiol or DMSO vehicle. After incubation for approximately 16 hours, the cells were refed EBM/BSA containing 30 U/ml IL-1β and either 100 nM 17β-estradiol or DMSO vehicle. After 5 hours incubation at 37° C., the cells were harvested using Trizol (Life Technologies). RNA was prepared according to the manufacturer's protocol. The purified total RNA was treated with 10 U Dnase I (Life Technologies) at 37™C for 1 hour and repurified by Rneasy spin columns (Qiagen; Chatsworth, Calif.).

Following DNase I treatment, six micrograms total RNA was incubated with 1×RT buffer (25 mM Tris-Cl, pH 8.3, 37.6 mM KCl, 3 mM $MgCl_2$ and 5 mM DTT, from Genhunter, Nashville, Tenn.), 20 µM dNTP's (A, C, G and TTP 2'-deoxynucleoside 5' triphosphates, Gibco/BRL), 0.2 µM $HT_{11}C$ (oligonucleotide: AAGCTTTTTTTTTTTC; SEQ ID NO: 8) in a final volume of 600 µL. This reaction mixture was incubated at 65° C. for five minutes to denature secondary structures, followed by a ten minute incubation at 37° C. 30 µl Superscript II reverse transcriptase (200U/µl, Gibco/BRL) was then added to the reaction and incubation proceeded for 1 hr at 37° C. The enzyme was inactivated by heating at 75° C. for five minutes. An aliquot of this reaction was then used for the second strand synthesis by PCR. To 2 µl of the reaction was added, 1×PCR buffer (10 mM Tris-Cl, pH 8.4, 100 mM KCl, 1.5 mM $MgCl_2$ and 0.001% gelatin), 2 µM dNTP's, 15 nM $^{33}P$ dATP (NEN), 1 unit AmpliTaq DNA polymerase (Perkin Elmer) and 1 µM arbitrary primer 5'-AAGCTTGCCATGG-3' (SEQ ID NO: 9) for a total reaction volume of 20 µl. This reaction mixture was then thermocycled using the following parameters:

92° C. for 2 min, 1 cycle,

92° C. for 15 sec, 40° C. for 2 min, 72° C. for 30 sec, 40 cycles

72° C. for 5 min

PCR products were separated by gel electrophoresis on a 6% denaturing polyacrylamide gel (5.7% acrylamide, 0.3% bisacrylamide, 42% urea and 51% $H_2O$) in 1×TBE buffer (0.1 M Tris, 0.09 M Boric Acid, 1 mM EDTA) for three hours at 2000 volts. The gel was then transferred to filter paper (Schleicher & Schuell), dried under vacuum at 80° C. for one hour and exposed to X-ray film for 24 hours. The developed film was then superimposed over the dried gel and the band of interest identified. Band corners were marked using a 22 gauge syringe needle and the gel slice within these boundaries excised with a razor blade and immersed in 100 µl $H_2O$. The sample was boiled in a water bath for fifteen minutes, centrifuged for two minutes and the supernatant solution transferred to a new tube. Added to this sample was 5 µl of 10 mg/ml glycogen, 10 µl of 3 M sodium acetate and 450 µl of 100% ethanol. The sample was mixed, allowed to precipitate overnight at −20° C. and centrifuged for ten minutes at 10,000 g. The supernatant solution was removed, the pellet washed with 200 µl of 85% ethanol, dried and resuspended in 10 µl $H_2O$. A 3 µl aliquot of this was used in a reamplification PCR reaction in the presence of 1×PCR buffer, 20 µM dNTP's, 0.2 µM arbitrary primer and 0.2 µM oligonucleotide $HT_{11}C$ and 2 units AmpliTaq polymerase using the same cycling parameters as the PCR reaction above.

Of the regulated bands identified, one band, #7, of approximately 320 bp in size, showed a very strong induction by 17β-estradiol treatment and was designated as endothelial estrogen regulated gene-7 (EER-7). The EER-7 fragment was cloned by TA cloning into the vector pCRII (InVitrogen). For Northern blot analysis, total RNA from HUVEC cells was fractionated by electrophoresis on a 1% (w/v) agarose gel at about 200 V for about 2 hours. The RNA was transferred to nylon membranes by capillary action overnight. The nylon membranes were hybridized with $^{32}$P-lableled EER-7 fragment cDNA probes prepared from gel purified EER-7 320 bp fragment using an oligonucleotide labeling kit (Pharmacia). The Northern results indicated that the full length EER-7 message was approximately 4.0 kb.

Analysis of the 320 bp sequence using the BLAST program (NCBI; non-redundant and EST databases) did not identify any homology to known genes but did reveal EST sequences (W42603, W44920, H25237 and AA166620) with homology. These ESTs were obtained from Research Genetics and sequenced in their entirety. The resulting sequence of approximately 1.2 kb did not have homology to known identified genes and did contain an identifiable coding region.

Figure 2:
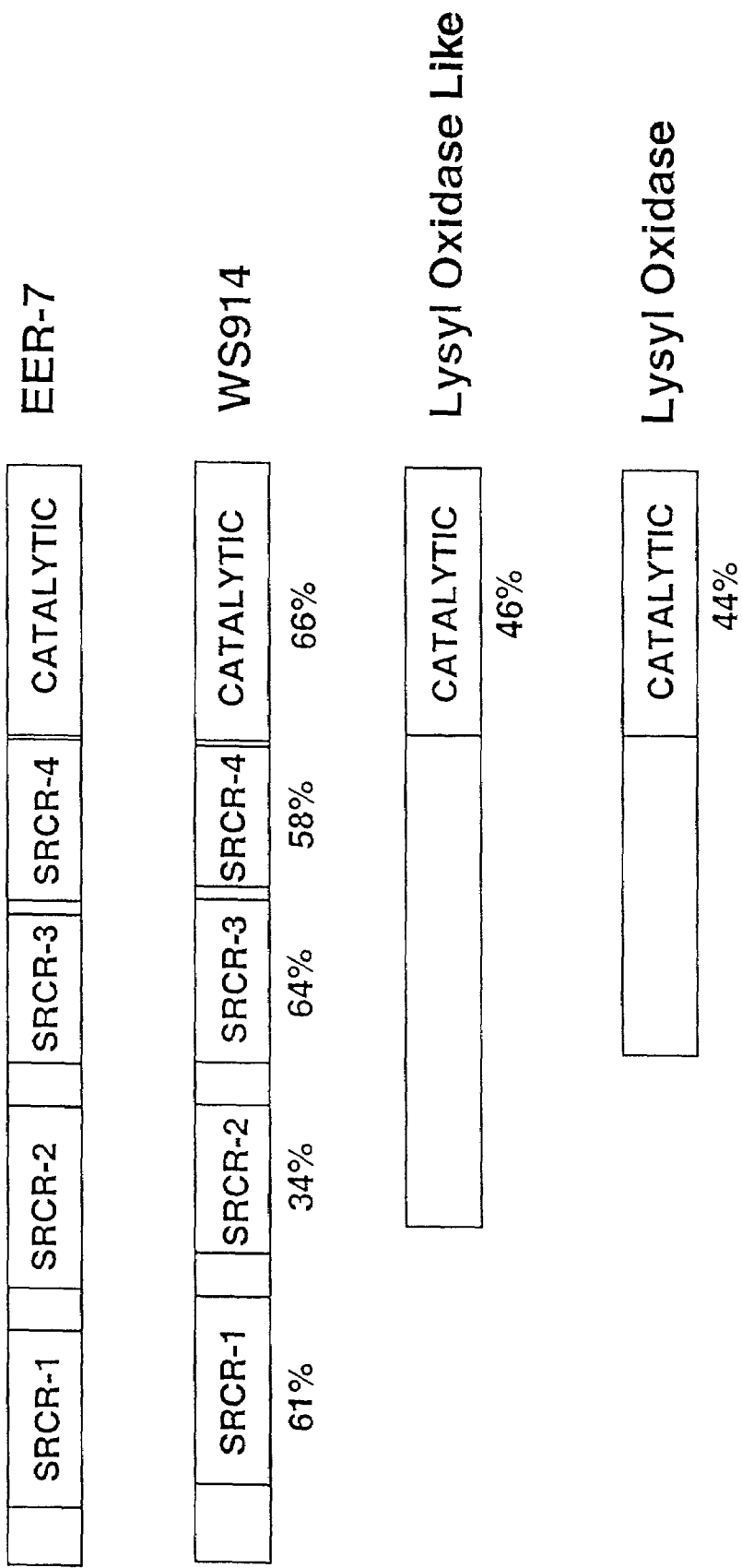
FIG. 2. Schematic representation of the sequence similarity of the SRCR and catalytic domains between the EER-7 protein and WS914, LOL, and LO proteins.

To isolate the EER-7 gene, a PCR screening approach (OriGene Rapid-Screen) was utilized with a human placenta library. Oligo primers derived from the known sequence of EER-7 (5'-TTTGCTCAGCTGAGCTCCT-3' and 5'-TAAGATAAAGGTAAGGACACTA-3'; SEQ ID NOS: 10 and 11, respectively) were first used in an RT-PCR reaction with human placenta total RNA. The predicted 340 bp band was observed following electrophoresis on a 1.2% agarose gel. The Origene 96-well human placenta library was then screened by PCR using these oligonucleotides. Five wells gave a 340 bp band. Sub-plates corresponding to these wells were obtained from Origene and a second round of PCR was performed to identify positive wells from each sub-plate. Positive subwells were plated onto LB+ampicillin plates to obtain individual colonies. These colonies were screened by colony hybridization (Sambrook et al., Molecular Cloning) using $^{32}$P-labeled 1 kb EST sequence as a probe. The membranes were hybridized overnight at 48° C. and then washed twice at room temperature with 2×SSC/0.5% SDS and twice at 60° C. with 0.1×SSC/0.1% SDS. Positive colonies were grown in LB+ampicillin and plasmid DNA was obtained (Qiagen). Plasmids were digested with EcoRI and SalI to release cDNA inserts. The reactions were subject to electrophoresis and Southern analysis as described for the colony hybridization protocol. The clone designated as D3E11 gave a cDNA insert of the expected size for a full length EER-7 clone and was sequenced in its entirety. BLAST analysis with this sequence identified similarity to known members of the lysyl oxidase family of genes (FIGS. 1 and 2).

Example 2

Regulation of EER-7 Expression

Human umbilical vein cells (HUVEC) were obtained as frozen stocks (Clonetics, San Diego, Calif.) at passage 2 or 3. Cells were maintained The cells were maintained in EBM medium supplemented with 10 ng/ml human EGF, 1 mg/ml hydrocortisone, 50 mg/ml gentamicin, 50 ng/ml amphotericin-B, 3 mg/ml bovine brain extract, and 2%, by volume, fetal bovine serum. The cells were used for experiments between passages 4 and 7.

Figure 3:
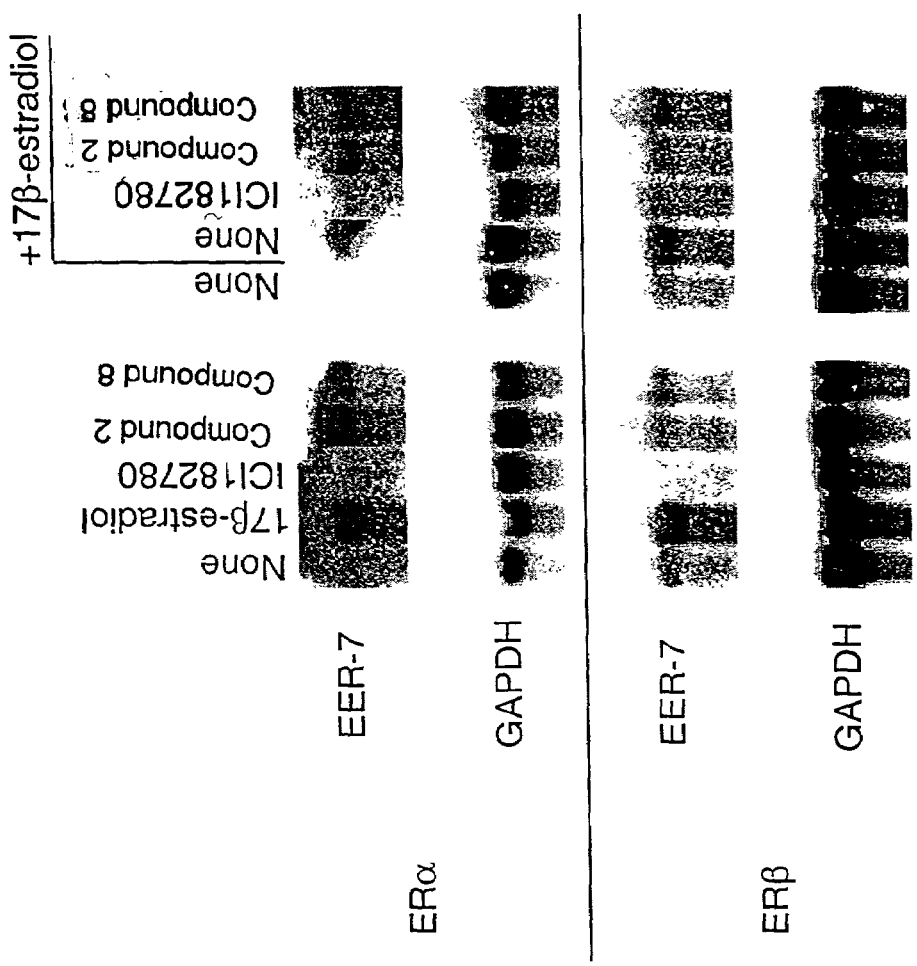
FIG. 3. Northern blots showing EER-7 and glyceraldehyde-3-phosphate dehydrogenase RNA levels after activation of ERα and ERβ receptors in HUVEC cells.

On day 0, HUVEC were plated in maintenance media at about $3 \times 10^6$ cells per 150 $mm^2$ plate. Cells were incubated at about 37° C. for about 24 hours. On day 1, cells were fed phenol red-free EBM media supplemented with 2%, by volume, charcoal/dextran treated fetal bovine serum (HyClone; Logan, Utah) and containing replication-defective adenovirus expressing human full length wild-type ERα (Ad5ERα) or ERβ (Ad5ERβ) at an approximate MOI of 300. Following infection, the cells were washed and refed with phenol red-free EBM media supplemented with 2%, by volume, charcoal/dextran treated fetal bovine serum. Cells were incubated at about 37° C. for about 20 hours. On day 3, total RNA was extracted from cells with silica gel columns (Qiagen, Chatsworth, Calif.). Total RNA was fractionated by electrophoresis on a 1% agarose gel at about 150 V for about 2 hours. RNA was transferred by capillary transfer using 20×SSC. Nylon membranes were hybridized with $^{32}$P-labeled EER-7 cDNA probes (generated using Pharmacia's Oligolabelling kit). Results are summarized in FIG. 3.

Sequence analysis of EER-7 indicated that the protein was structurally similar to other proteins that belong to the LO and LOL protein family (see FIG. 1). Comparison of the domains indicates that EER-7 shares the characteristic catalytic domain associated with LO and LOL proteins and also contains four SRCR domains, which are present in WS914. Combined, this indicates that EER-7 protein may play a role in cellular signalling pathways through protein-protein interactions mediated by the SRCR domains.

Figure 4:
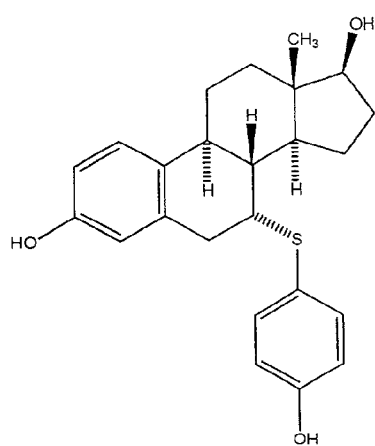
FIG. 4. Structures of compounds 2 and 8.
Figure 4:
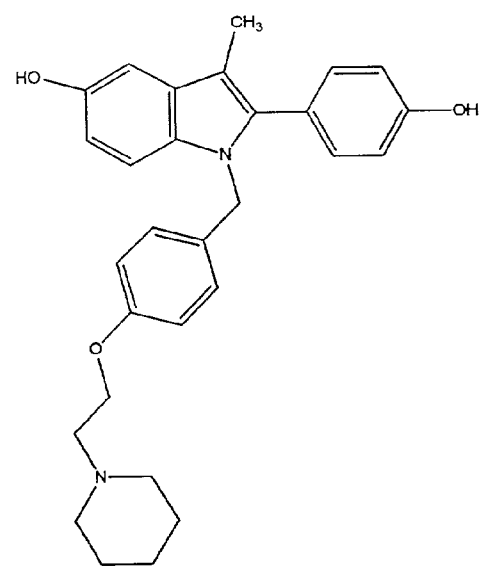

Expression studies indicated that EER-7 expression was regulated by both the ERα and ERβ receptors in HUVEC cells. The prototypical estrogen agonist 17β-estradiol stimulated EER-7 expression through interaction with both receptors. Additionally, this effect was blocked by the non-selective estrogen receptor antagonist IC182780 (see FIG. 3, right hand panels). The ERα agonists and ERβ antagonists, Compounds 2 and 8 (FIG. 4) both stimulated EER-7 expression through the ERα and blocked the effects of 17β-estradiol at the ERβ receptor. These studies indicate that the EER-7 expression and activity are modulated by both estrogen receptors, Therefore, estrogen mediated modulation of EER-7 may represent a new avenue of development for therapeutic strategies for AAAs and myocardial infarctions.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

All patents, patent applications, publications, and other materials cited herein are hereby incorporated herein reference in their entireties.

What is claimed is:

1. An isolated nucleic acid encoding an endothelial estrogen regulated gene-7 protein that has (i) an amino acid sequence which has at least about 95% sequence similarity with SEQ ID NO: 2 and (ii) lysyl oxidase activity.

2. The isolated nucleic acid of claim 1, wherein the endothelial estrogen regulated gene-7 protein comprises four scavenger receptor cysteine rich (SRCR) domains having an amino acid sequence at least about 95% identical to the amino acid sequences of SEQ ID NOs: 3, 4, 5, and 6.

3. The isolated nucleic acid of claim 2, wherein the endothelial estrogen regulated gene-7 protein comprises four scavenger receptor cysteine rich domains having the amino acid sequences of SEQ ID NOs: 3, 4, 5, and 6.

4. The isolated nucleic acid of claim 1, which is a cDNA.

5. The isolated nucleic acid of claim 1, wherein the endothelial estrogen regulated gene-7 protein has the amino acid sequence of SEQ ID NO: 2.

6. The isolated nucleic acid of claim 5, which is a cDNA.

7. The isolated nucleic acid of claim 5, which comprises the nucleotide sequence of SEQ ID NO: 1.

8. The isolated nucleic acid of claim 7, which is a cDNA.

9. A vector comprising the isolated nucleic acid of claim 1.

10. A vector comprising the isolated nucleic acid of claim 2.

11. A vector comprising the isolated nucleic acid of claim 5.

12. A vector comprising the isolated nucleic acid of claim 7.

13. The vector of claim 9, wherein the endothelial estrogen regulated gene-7 protein is expressed in response to estrogen.

14. An isolated host cell transfected with the vector of claim 9.

15. An isolated host cell transfected with the vector of claim 10.

16. An isolated host cell transfected with the vector of claim 11.

17. An isolated host cell transfected with the vector of claim 12.

18. A method for producing endothelial estrogen regulated gene-7 protein, which method comprises isolating the endothelial estrogen regulated gene-7 protein produced by the host cell of claim 14, wherein the host cell has been cultured under conditions that provide for expression of the endothelial estrogen regulated gene-7 protein by the vector.

19. A method for producing endothelial estrogen regulated gene-7 protein, which method comprises isolating the endothelial estrogen regulated gene-7 protein produced by the host cell of claim 15, wherein the host cell has been cultured under conditions that provide for expression of the endothelial estrogen regulated gene-7 protein by the vector.

20. A method for producing endothelial estrogen regulated gene-7 protein, which method comprises isolating the endothelial estrogen regulated gene-7 protein produced by the host cell of claim 16, wherein the host cell has been cultured under conditions that provide for expression of the endothelial estrogen regulated gene-7 protein by the vector.

21. A method for producing endothelial estrogen regulated gene-7 protein, which method comprises isolating the endothelial estrogen regulated gene-7 protein produced by the host cell of claim 17, wherein the host cell has been cultured under conditions that provide for expression of the endothelial estrogen regulated gene-7 protein by the vector.

22. An isolated oligonucleotide primer or probe of 50–100 nucleotides, wherein said oligonucleotide comprises at least 20 consecutive nucleotides of SEQ ID NO: 1 and hybridizes under highly stringent conditions of 0.2×SSC at 68° C. and a washing condition of 50% formamide, 4×SSC at 42° C. with a nucleic acid having the nucleotide sequence of SEQ ID NO: 1.

23. The isolated oligonucleotide primer or probe of claim 22, which is no more than 60 nucleotides in length.

24. The isolated oligonucleotide primer or probe of claim 22, which is no more than 50 nucleotides in length.

25. The isolated oligonucleotide primer or probe of claim 22 which is detectably labeled.

26. An isolated oligonucleotide primer or probe of 100 nucleotides, wherein said oligonucleotide comprises at least 20 consecutive nucleotides of SEQ ID NO: 1 and hybridizes under highly stringent conditions of 0.2×SSC at 68° C. and a washing condition of 50% formamide, 4×SSC at 42° C. with a nucleic acid having the nucleotide sequence of SEQ ID NO: 1.

* * * * *